(12) United States Patent
Patel et al.

(10) Patent No.: US 9,870,451 B1
(45) Date of Patent: Jan. 16, 2018

(54) DYNAMIC MANAGEMENT, ASSEMBLY, AND PRESENTATION OF WEB-BASED CONTENT

(71) Applicant: Emmi Solutions, LLC, Chicago, IL (US)

(72) Inventors: Nimesh Patel, Chicago, IL (US); Greg Blew, Glen Ellyn, IL (US); Paul Landes, Oak Park, IL (US)

(73) Assignee: Emmi Solutions, LLC, Chicago, IL (US)

(*) Notice: Subject to any disclaimer, the term of this patent is extended or adjusted under 35 U.S.C. 154(b) by 479 days.

(21) Appl. No.: 14/695,542

(22) Filed: Apr. 24, 2015

Related U.S. Application Data

(60) Provisional application No. 62/084,439, filed on Nov. 25, 2014.

(51) Int. Cl.
*G06F 15/16* (2006.01)
*G06F 19/00* (2011.01)
*H04L 29/08* (2006.01)

(52) U.S. Cl.
CPC .......... *G06F 19/3487* (2013.01); *H04L 67/12* (2013.01)

(58) Field of Classification Search
CPC .............. G06F 19/322; G06F 19/3418; G06F 19/3487; G06F 21/6245; G06F 19/324; H04L 67/12
USPC ........................................................ 709/217
See application file for complete search history.

(56) References Cited

U.S. PATENT DOCUMENTS

| 6,567,829 | B1 | 5/2003 | Ter Horst et al. |
| 8,214,518 | B1 | 7/2012 | Bertz |
| 8,818,260 | B2* | 8/2014 | Gaines .................. H04W 40/02 455/11.1 |
| 2002/0080387 | A1* | 6/2002 | Grasso .............. G06F 17/30011 358/1.15 |
| 2004/0117839 | A1 | 6/2004 | Watson et al. |
| 2004/0122539 | A1 | 6/2004 | Ainsworth |

(Continued)

OTHER PUBLICATIONS

Adobe Developer Connection, "Creating your first Flash Professional CS5 document," (2010). Retrieved from the Internet on Mar. 10, 2015: <URL:https://adobe.com/devnet/flash/articles/flash_cs5_createfla.html>.

(Continued)

*Primary Examiner* — Phuoc Nguyen

(74) *Attorney, Agent, or Firm* — Marshall, Gerstein & Borun LLP

(57) ABSTRACT

In a method for seamlessly providing health-related information, a patient presentation is identified. Each of at least some presentation nodes is selectively activated or not activated for a particular instance of the presentation, and corresponds to respective content assets to be presented if the node is activated. A first node sequence to be activated for an instance of the presentation is determined. First content to be at least partially presented during a first portion of the instance is identified based on the first node sequence, and sent to a client device. A message indicating when the client device is ready for additional content is received, and a second node sequence to be activated for the instance is determined. Second content that is to be at least partially presented during a second portion of the instance is identified based on the second node sequence, and sent to the client device.

20 Claims, 11 Drawing Sheets

(56) References Cited

U.S. PATENT DOCUMENTS

| | | |
|---|---|---|
| 2008/0098319 A1 | 4/2008 | Lucas |
| 2008/0103371 A1 | 5/2008 | Rosenblum et al. |
| 2008/0140719 A1 | 6/2008 | Chaney et al. |
| 2009/0327895 A1 | 12/2009 | Bailloux et al. |
| 2010/0268740 A1* | 10/2010 | Barker .............. G06F 17/30011 707/783 |
| 2017/0249290 A1* | 8/2017 | Maksimov .......... G06F 17/2288 |

OTHER PUBLICATIONS

U.S. Appl. No. 14/712,590, filed May 14, 2015, titled "Environment for Designing a Dynamic Multimedia Content Presentation".
U.S. Appl. No. 14/732,246, filed Jun. 5, 2015, titled "Multiple Delivery Channels for a Dynamic Multimedia Content Presentation".

* cited by examiner

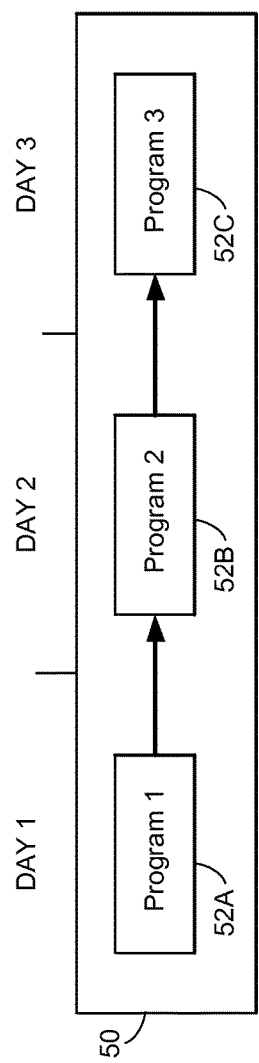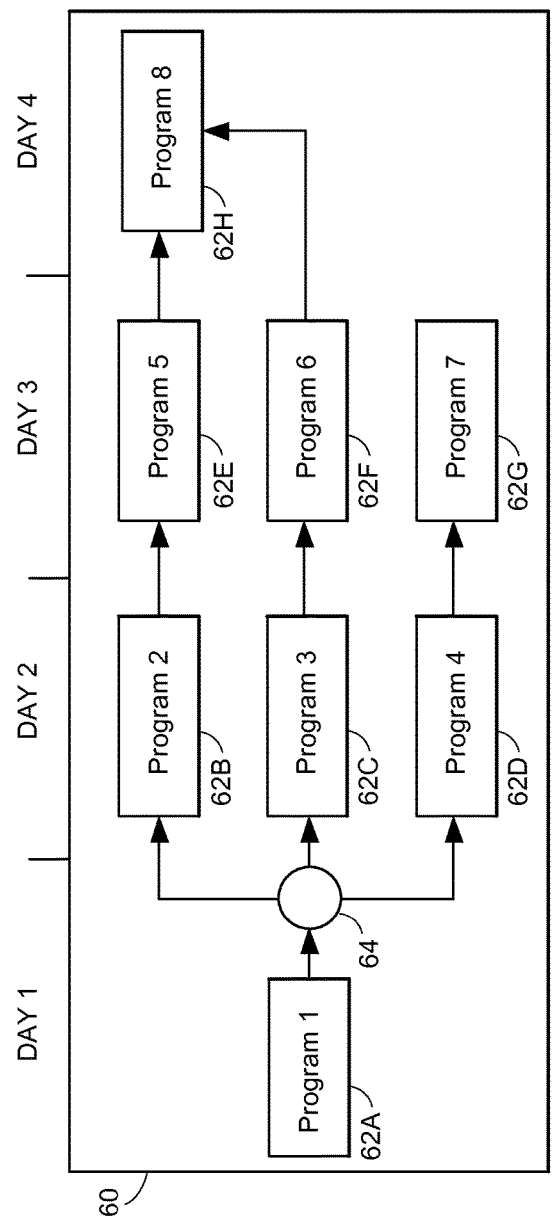

DYNAMIC MANAGEMENT, ASSEMBLY, AND PRESENTATION OF WEB-BASED CONTENT

CROSS-REFERENCE TO RELATED APPLICATION

This application claims priority to and benefit of U.S. Provisional Application Ser. No. 62/084,439, entitled "Environment For Designing A Dynamic Multimedia Content Presentation" and filed on Nov. 25, 2014, the disclosure of which is hereby incorporated by reference herein in its entirety.

FIELD OF THE INVENTION

The present disclosure generally relates to dynamic network-based multimedia content presentations.

BACKGROUND

In the healthcare industry, educating patients, and obtaining information from patients, is critical to ensuring patient satisfaction and high quality patient care. For example, many clinical flows require adequately informing the patient (e.g., regarding medical procedures, medical conditions, and/or other matters), gathering information from the patient (e.g., information regarding how the patient feels, demographic information for the patient, health-related habits of the patient, etc.), taking certain actions with respect to the patient (e.g., scheduling a follow-up appointment), and so on.

Unfortunately, it can sometimes be difficult to provide a patient with relevant information, and to obtain the information needed from the patient. In a typical scenario, for example, a patient receives information during a live, in-person appointment. Alternatively, a patient may receive information during a phone conversation with a live medical professional. These conventional approaches have several drawbacks. For example, the patient may find it difficult to visit his or her doctor's office for various reasons (e.g., work, childcare, etc.), and/or it may be difficult to get a hold of the patient by telephone. Moreover, human error might at times result in the patient not receiving important information. Still further, because there are typically no records of precisely what was said to a patient (e.g., during doctor office visits and telephone calls with the doctor or staff members), liability issues may arise in various contexts, such as whether the patient truly gave "informed consent."

While healthcare information, or surveys requesting patient information, may at times be electronically provided to patients, the information or questions are typically not customized to the patient or the patient's situation. For example, the patient may simply be provided with an "information dump" that includes everything that may be of relevance, or the patient may be asked to complete an electronic survey that asks a fixed set of questions regardless of whether particular questions are relevant to that patient. These approaches, too, may have significant drawbacks. For example, the patient may be required to wade through an unnecessarily large amount of information and/or number of questions.

SUMMARY

In one aspect, a method for seamlessly providing health-related information to an end-user comprises identifying, at one or more servers, a patient presentation for the end-user. The patient presentation is associated with (i) a set of rules and (ii) a plurality of nodes. Each of at least some of the plurality of nodes is selectively activated, or selectively not activated, for a particular instance of the patient presentation in accordance with the set of rules when operating upon a set of facts, and corresponds to one or more respective content assets that are to be presented to the end-user if and only if the node is activated. The method also includes determining, at the one or more servers, a first node sequence to be activated for a first instance of the patient presentation. The first node sequence includes a first subset of the plurality of nodes. The method also includes identifying, at the one or more servers and based on at least the first node sequence, first content that is to be at least partially presented to the end-user during a first portion of the first instance of the patient presentation. The first content includes the respective content assets that correspond to the first subset of the plurality of nodes. The method also includes sending, from the one or more servers, the first content to a client device via a network; receiving, at the one or more servers and from the client device, a message indicating when the client device is ready for additional content of the patient presentation; and determining, at the one or more servers and using at least (i) a first rule of the set of rules and (ii) a first fact of the set of facts, a second node sequence to be activated for the first instance of the patient presentation. The second node sequence includes a second subset of the plurality of nodes. The method also includes identifying, at the one or more servers and based on at least the second node sequence, second content that is to be at least partially presented to the end-user during a second portion of the first instance of the patient presentation. The second content includes at least a portion of the respective content assets that correspond to the second subset of the plurality of nodes. The method also includes sending, from the one or more servers and after receiving the message, the second content to the client device via the network.

In another aspect, a system for seamlessly providing health-related information to an end-user comprises one or more processors, and one or more memories storing instructions that, when executed by the one or more processors, cause the one or more processors to identify a patient presentation for the end-user. The patient presentation is associated with (i) a set of rules and (ii) a plurality of nodes. Each of at least some of the plurality of nodes is selectively activated, or selectively not activated, for a particular instance of the patient presentation in accordance with the set of rules when operating upon a set of facts, and corresponds to one or more respective content assets that are to be presented to the end-user if and only if the node is activated. The instructions also cause the one or more processors to determine a first node sequence to be activated for a first instance of the patient presentation. The first node sequence includes a first subset of the plurality of nodes. The instructions also cause the one or more processors to identify, based on at least the first node sequence, first content that is to be at least partially presented to the end-user during a first portion of the first instance of the patient presentation. The first content includes the respective content assets that correspond to the first subset of the plurality of nodes. The instructions also cause the one or more processors to send the first content to a client device via a network; receive from the client device a message indicating that the client device is ready for additional content of the patient presentation; and determine, using at least (i) a first rule of the set of rules and (ii) a first fact of the set of facts, a second node sequence to be activated for the first instance of the patient presentation. The second node sequence includes a second subset of the plurality of nodes. The instructions also cause the one or more processors to identify, based on at least the second node sequence, second content that is to be at least partially presented to the end-user during a second portion of the first instance of the patient presentation. The second content includes at least a portion of the respective content assets that correspond to the second subset of the plurality of nodes. The instructions also cause the one or more processors to send the second content to the client device via the network.

In another aspect, a system comprises a client device associated with an end-user, a first data storage storing a knowledge base that includes a set of rules and a set of facts both associated with a patient presentation, and a second data storage storing a plurality of content assets for a plurality of nodes associated with the patient presentation. Each of at least some of the plurality of nodes (i) is selectively activated, or selectively not activated, for a particular presentation of the patient presentation in accordance with the set of rules when operating upon the set of facts, and (ii) corresponds to one or more respective content assets, of the plurality of content assets, that are to be presented to the end-user if and only if the node is activated. The system also includes one or more servers configured to (i) determine a first node sequence to be activated for a first instance of the patient presentation, the first node sequence including a first subset of the plurality of nodes; (ii) identify, based on at least the first node sequence, first content that is to be at least partially presented to the end-user during a first portion of the first instance of the patient presentation, the first content including the respective content assets that correspond to the first subset of the plurality of nodes; and (iii) send the first content to the client device via a network. The client device is configured to (i) assemble the first content during the first instance of the patient presentation, (ii) present at least a portion of the assembled first content to the end-user, and (iii) prior to an entirety of the portion of the first content being presented to the end-user, send the one or more servers a message indicating when the client device is ready for additional content of the patient presentation. The one or more servers are further configured to, after receiving the message indicating when the client device is ready for additional content, (i) determine, using at least a first rule of the set of rules and a first fact of the set of facts, a second node sequence to be activated for the first instance of the patient presentation, the second node sequence including a second subset of the plurality of nodes; (ii) identify, based on at least the second node sequence, second content that is to be at least partially presented to the end-user during a second portion of the first instance of the patient presentation, the second content including at least a portion of the respective content assets that correspond to the second subset of the plurality of nodes; and (iii) send the second content to the client device via the network. The client device is further configured to (i) assemble the second content during the first instance of the patient presentation, and (ii) present at least a portion of the assembled second content to the end-user.

BRIEF DESCRIPTION OF THE DRAWINGS

FIG. 2 depicts an example interactive media pack (IMP), according to an embodiment.

FIG. 3 depicts another example IMP, according to an embodiment.

DETAILED DESCRIPTION

I. Overview

Figure 1:
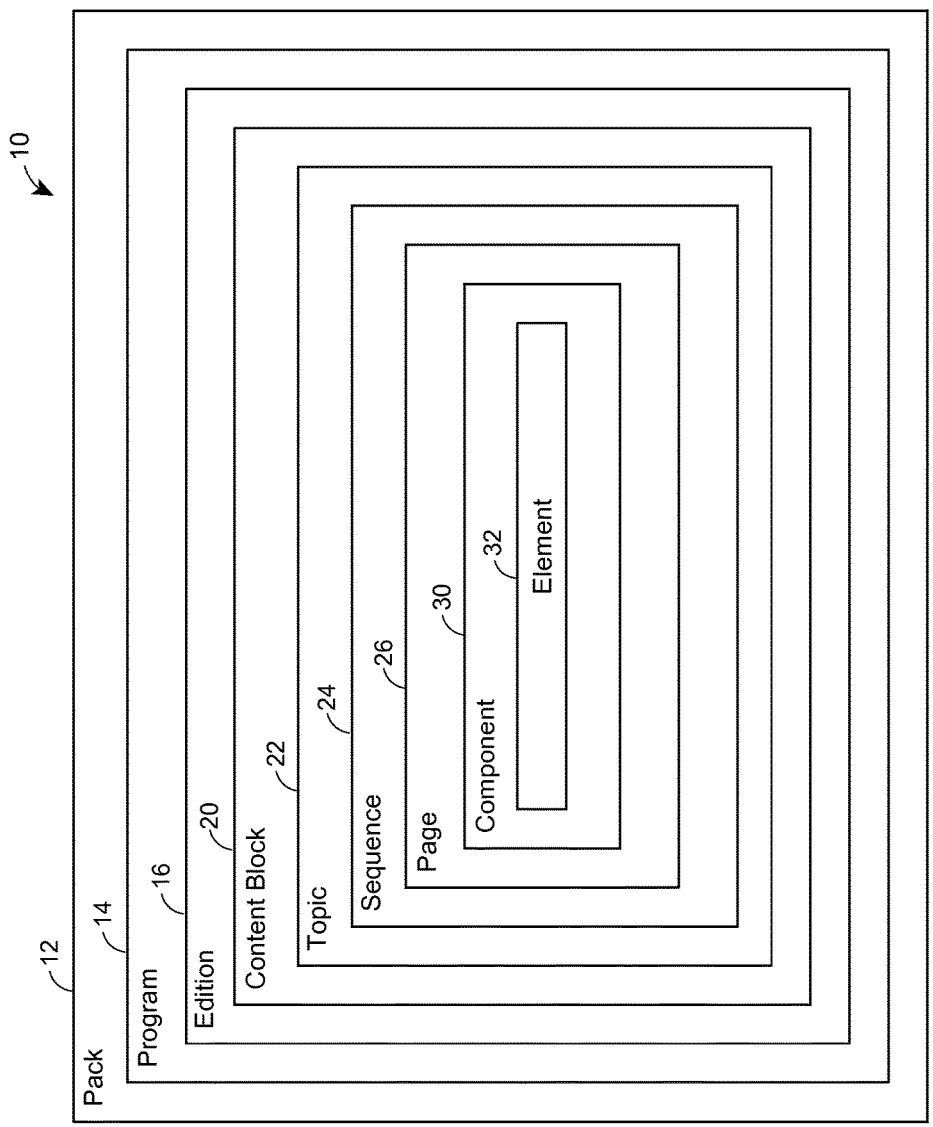
FIG. 1 depicts an example hierarchy in which dynamic, multimedia content for a patient may be arranged, according to an embodiment.

In embodiments described below, an interactive media pack (IMP) may present multimedia, healthcare-related content to a patient or other end-user via a client/computing device (e.g., the patient's smartphone, tablet, laptop or desktop computer, etc.). The IMP may have been "prescribed" by a healthcare professional, for example. The IMP may be interactive in nature, allowing the end-user to interact with the presented content. For example, the IMP may prompt the end-user to answer various questions during a presentation of the IMP. The IMP may also be dynamic in nature. For example, an IMP may include various nodes that may be selectively activated or executed, where each node, if and when activated, may present to the end-user a certain subset of the multimedia content associated with the IMP. Which nodes are activated, and/or the order in which the nodes are activated, may be determined, in whole or in part, during run-time. Accordingly, the particular sequence in which the multimedia content is presented to the end-user may not be known prior to the IMP being initiated.

The conditional logic that is used to decide which nodes of an IMP should be next activated may be embodied by "rules." These rules may take any of a number of forms, but generally speaking, may be any information or data that can be referenced for determining what node should be next activated. In an embodiment, one or more of the rules may reside at a third party system. Further, the one or more rules may be implemented, in whole or in part, by a third party system. In other embodiments, none of the rules reside at a third party system, and/or are not implemented by third party systems. To illustrate, the rules may be implemented by a rules engine. Generally speaking, a rules engine is a system configured to select a next node to be activated, for example, according to the rules (i.e., according to logic embodied by the rules) and/or according to other data or information (e.g., "facts"). In an embodiment, the rules engine is implemented, in whole or in part, by a third party. In other embodiments, the rules engine is not implemented by a third party. Regardless of the exact manner of implementation, the rules engine may select a next node for activation according to the rules.

The rules may specify one or more conditions and a particular node to activate when these one or more conditions exists. The existence or non-existence of these conditions may depend on the existence or non-existence of one or more "facts." Thus, to evaluate each condition specified by the rules, the rules engine may access facts stored in a knowledge base and may determine the appropriate node(s) to activate, during run-time, by way of the rules operating on those facts. To illustrate, a rule may stipulate "activate Node X if today is a Tuesday." The condition "today is a Tuesday" depends on a fact: what day of the week "today" actually is. In such an example, the rules engine may access facts in the knowledge base to evaluate the condition "today is a Tuesday," and may activate Node X when the condition is true.

The facts may represent information that was previously provided by the end-user (e.g., in response to user prompts presented earlier within the IMP), and/or information that was collected from other sources (e.g., electronic medical records, patient registry software, prescription software, biometric devices worn by patients, etc.), for example.

The term "nodes," as used herein, may generally refer to units of content of any size or duration, or of variable size and/or duration, within an IMP, and/or to decision points that connect other nodes within the IMP. The IMP and its nodes may be arranged according to various different configurations or hierarchies, such as a flat configuration, or a hierarchy with nodes at multiple layers (e.g., nodes within nodes). For instance, nodes within one layer of an IMP may include different "programs" that broadly serve different purposes within the IMP (e.g., obtaining advanced directives, obtaining informed consent, facilitating decision-making with respect to a particular health condition, etc.), nodes within a lower layer of the IMP may include different "content blocks" or "chapters" that serve different, more specific purposes within programs (e.g., informing a patient/end-user about a specific subject or asking the patient a subset of questions associated with a subject, etc.), and nodes within a still lower layer of the IMP may include different "pages" that are to be displayed/presented to the end-user within the content blocks or chapters. One example hierarchy, including still more layers, is described below in Section II.

In some embodiments, the dynamic/selective activation (or non-activation) of nodes discussed above occurs within each of multiple hierarchy layers. Referring to the hierarchy examples above (IMP, program, content block, page), for instance, conditional logic may be applied at run-time to determine which page is to be presented next within a particular content block. Similarly, other conditional logic may be applied at run-time to determine which content block is to be presented next within a particular program. Each hierarchy layer may or may not be transparent to the end-user (e.g., depending on whether the presented content includes information that demarks the different nodes within each layer, such as program names, chapter titles, etc.).

Depending on the embodiment, the conditional logic within various layers of an IMP may be understood as a particular type (or category) of conditional logic. For example, the conditional logic may be embodied by rules that facilitate scheduling, and/or rules that facilitate conditional branching. Scheduling may involve activating a node or nodes (and potentially an order for said activation) based on one or more factors (e.g., events or triggers not necessarily expected to occur at any particular time). Conditional branching may involve evaluating conditions at a particular point during execution of an IMP (e.g., at an expected decision-point) to identify a next node for activation from multiple potential nodes. Facts or factors upon which rules for scheduling and/or conditional branching can be based may include, for example: what doctors prescribe to patients; temporal-based events based on schedule, such as reminder calls to watch a program, collect feedback, etc.; special rules and configurations by the hospital or clinic; chaining programs together for illnesses that are related; workflow automation in the context of the above and the extent to which other tasks integrate with other systems (e.g., call systems); information contained within (or derived from) end-user feedback that was provided in response to a user prompt presented earlier in a particular program; etc.

Generally, portions of an IMP may, in some embodiments, be presented to the end-user via one communication channel, or via multiple communication channels. For example, a first program within a particular IMP may include multimedia content that is presented to the end-user via a web browser of the end-user's computing device, while a second program of the IMP may include a survey presented to the end-user via email (or via a telephone call using interactive voice response (IVR) technology, etc.). In other embodiments, the entire IMP may be presented to the end-user via a single communication channel.

Presenting dynamic multimedia content of an IMP to the end-user creates various challenges with respect to offering the end-user a seamless user experience. If Adobe Flash files (for a desktop computer) or MP4 files (for mobile devices) are used to provide content for a dynamic presentation within an IMP, for example, it may be necessary to download all of the content, associated with all of the potential/alternative pathways of the presentation, before the end-user even begins the presentation. For presentations with a large amount of multimedia content, this may create issues with inadequate buffering/data storage (particularly for mobile devices), and/or long delays at the outset as the end-user waits for the entire download to complete.

In some embodiments, to reduce or avoid delays, and/or to avoid downloading and/or buffering an entire presentation (IMP or IMP portion) before initiating the presentation, instructions that specify the structure and presentation of the multimedia content may be provided to the end-user device in a HyperText Markup Language version 5 (HTML5) format. The end-user device may then assemble the received content substantially in real-time during the presentation, as the content is received, and present the content via an HTML5-capable web browser in accordance with the HTML5 instructions.

To further ensure a seamless/smooth user experience and reduce buffering requirements, the end-user device may execute a multi-thread process, with a first thread being responsible for requesting and/or obtaining content (e.g., from a content server) when the end-user device is ready for additional content, and a different, second thread being responsible for consuming the content that has already been provided (e.g., assembling the content in real-time as that content is produced by the first thread). A content server providing the content to the end-user device may decide which content to provide based on the upcoming node sequence (e.g., a node sequence identified by the rules engine during the presentation, as discussed above), and possibly also based on one or more other criteria, algorithms or factors dictating how much content should be provided (e.g., a maximum byte size of a next "chunk" of content that is to be sent to the end-user device). In some embodiments and/or scenarios, to reduce the possibility of presentation delays, some of the content provided within a particular "chunk" of content may include content corresponding to two or more alternative node sequences (e.g., at least an initial node of each of three alternative sequences, each sequence being a possible choice by the rules engine when a particular condition or rule is evaluated at a decision point).

II. Example IMP Configurations

FIG. 1 depicts an example hierarchy 10 for an IMP 12, according to an embodiment. The hierarchy 10 includes a program layer 14 with one or more programs of the IMP 12, an edition layer 16 with one or more editions per program, a content block layer 20 with one or more content blocks per edition, a topic layer 22 with one or more topics per content block, a sequence layer 24 with one or more sequences per topic, a page layer 26 with one or more pages per sequence, a component layer 30 with one or more components per sequence, and an element layer 32 with one or more elements per component.

Generally, the IMP 12 may be directed to any type of subject matter, and may serve any type of purpose or purposes relating to that subject matter. For example, the IMP 12 may be designed to facilitate steps of a clinical flow associated with a particular type of medical treatment, therapy or condition. Within the program layer 14, each program may have a particular high-level function, such as obtaining and documenting informed consent (e.g., prior to a surgical procedure for the end-user/patient), obtaining and documenting an advanced directive (e.g., to specify what action should be taken if the end-user/patient is unable to make informed decisions due to health/incapacity issues), providing support for treatment and/or medication decisions, a mix of two or more such functions, etc.

Each of one, some or all of the programs within the program layer 14 may be associated with multiple editions in the edition layer 16. Each edition within a particular program may correspond to a different type of communication channel that is used to convey the program to the end-user. A "communication channel" for a particular edition may refer to the file format of the program content, the file format of instructions specifying the structure and presentation of the program content, and/or the type of end-user device needed to present the program content, for example. To provide some more specific examples, a first edition may correspond to an HTML5 edition of the program intended for presentation on a device with an HTML5-capable browser, a second edition may correspond to an Adobe Flash version of the program intended for presentation on a laptop or desktop computer, a third edition may correspond to an SMS text version of the program intended for presentation on a mobile phone device, a fourth edition may correspond to an IVR version of the program intended for presentation via a mobile or landline phone, and so on. Of course, some types of editions/communication channels may be unsuitable for particular programs (e.g., an IVR edition may be unsuitable for a program that heavily relies on video content), and/or some or all programs within the program layer 14 may only be associated with a single edition.

Each content block within the content block layer 20 may have a particular function, such as providing background information to the end-user, collecting information from the end-user (e.g., demographic information, information reflecting a self-assessment of symptoms, etc.), providing results to the end-user (e.g., based on information that the end-user entered earlier in the program), taking a particular action (e.g., scheduling a follow-up appointment, providing or setting up a reminder, sending results to healthcare professionals, etc.), a mix of two of more such functions, or any other suitable function.

Each topic within the topic layer 22 may have a more specific function within its respective/parent content block, such as providing a particular subset of background information to the end-user, collecting a particular subset of information from the end-user, etc. In some embodiments, topics may be the only divisions of an IMP that are noticeable to the end-user, with all other layers of the hierarchy 10 being transparent to the end-user.

Each sequence of the sequence layer 24 may contain an animation, a series of images and/or text, and/or other temporally-varying visual and/or audio content. A single sequence may contain a number of pages from the page layer 26, where each page arranges one or more components in the component layer 30 according to a layout specific to that page. In some embodiments, the layout of each page is dependent on the display capabilities of the end-user device (e.g., the aspect ratio of the display screen). Each component of a page may be a collection of one or more visual and/or audio elements within the element layer 32 (e.g., blocks of text, snippets of audio or video, etc.).

Some of the nodes/units within one or more of the layers of the example hierarchy 10 may be reusable. For example, a content management system may store a number of different topics, each of which can be retrieved and plugged into different content blocks and/or different IMPs. As another example, the content management system may store a number of different content blocks, each of which can be retrieved and plugged into different programs and/or different IMPs.

It is understood that, in other embodiments/implementations, the hierarchy 10 may include more, fewer and/or different layers than those shown in FIG. 1. Moreover, a single IMP may be viewed as having multiple different hierarchical configurations (e.g., by grouping the content of the IMP in various different ways).

FIGS. 2-6 depict example IMPs, or portions of example IMPs, according to various embodiments and/or design choices. The various configurations/hierarchies shown in FIGS. 2-6 may be design choices made by an IMP author using any of the authoring systems, tools and/or techniques described in U.S. Provisional Application Ser. No. 62/084, 439, for example. It is understood that, in different embodiments and/or designs, the configurations and/or hierarchical structures of FIGS. 2-6 may be different than shown.

Referring first to FIG. 2, and example IMP 50 includes three programs 52A-52C, with each of the programs 52 being scheduled for presentation to the end-user on a different day. As seen in FIG. 2, each of the programs 52 may be scheduled to be presented unconditionally. One or more of the programs 52 may, however, include lower-layer nodes/units (e.g., content blocks, topics, etc.) that are selectively activated or not activated according to conditional logic implemented by a rules engine.

FIG. 3 depicts a somewhat more complex IMP 60 that includes eight programs 62A-62H, with each of the programs 62A-62H being scheduled for presentation to the end-user on a different day. Unlike the IMP 50 of FIG. 1, however, some of the programs 62 are not activated for a particular instance of the IMP 60. In particular, as seen in FIG. 3, it is determined at a decision point/node 64 whether a particular instance of the IMP 60 will include programs, in addition to program 62A, programs 62B, 62E and 62H; programs 62C, 62F and 62H; or 62D and 62G. The decision point 64 may correspond to conditional logic as expressed by one or more rules of a rules engine. The rule(s) evaluated at decision point 64 may operate on facts based on information the end-user had entered during the program 62A, or information from any of various other sources (e.g., any of the data sources discussed below in connection with Section V).

Figure 4:
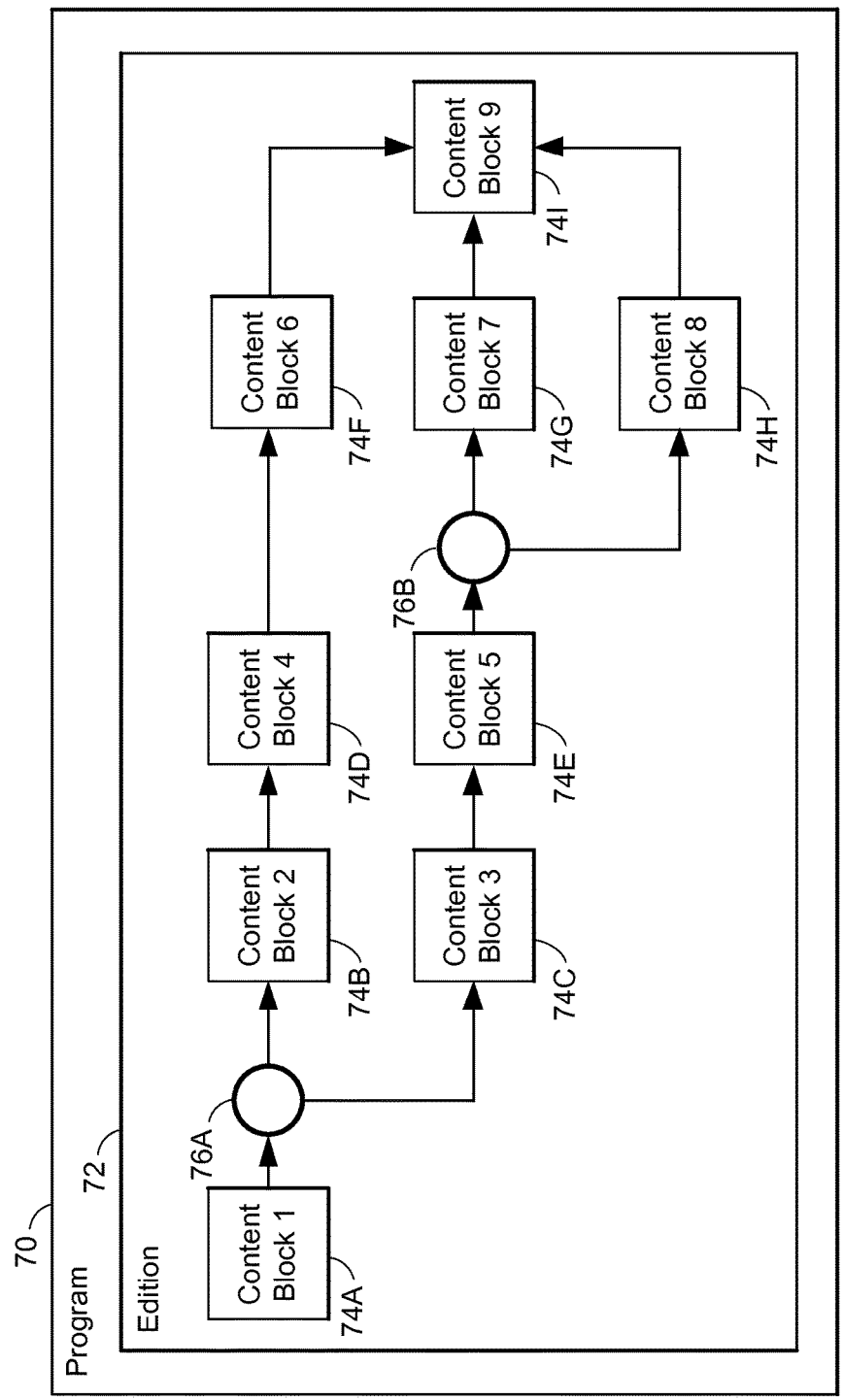
FIG. 4 depicts an example program (e.g., within an IMP), according to an embodiment.

FIG. 4 depicts an example program 70, which may correspond to one of the programs 52 of IMP 50 in FIG. 2, one of the programs 62 of IMP 60 in FIG. 3, or a program within a different IMP, for instance. The program 70 includes an edition 72, which may correspond to a particular communication channel (e.g., web-based provision of content with HTML5 instructions). The program 70 may also include one or more additional editions corresponding to different communication channels (e.g., Flash, etc.). The example edition 72 includes nine content blocks 74A-74I, and two decision points 76A and 76B. As seen in FIG. 4, content blocks 74A and 74I are activated for each and every presentation/instance (so long as the edition 72 of the program 70 is completed from beginning to end), whereas content blocks 74B-74H are only conditionally activated depending on the results of the evaluations at decision point 76A and/or 76B.

Figure 5:
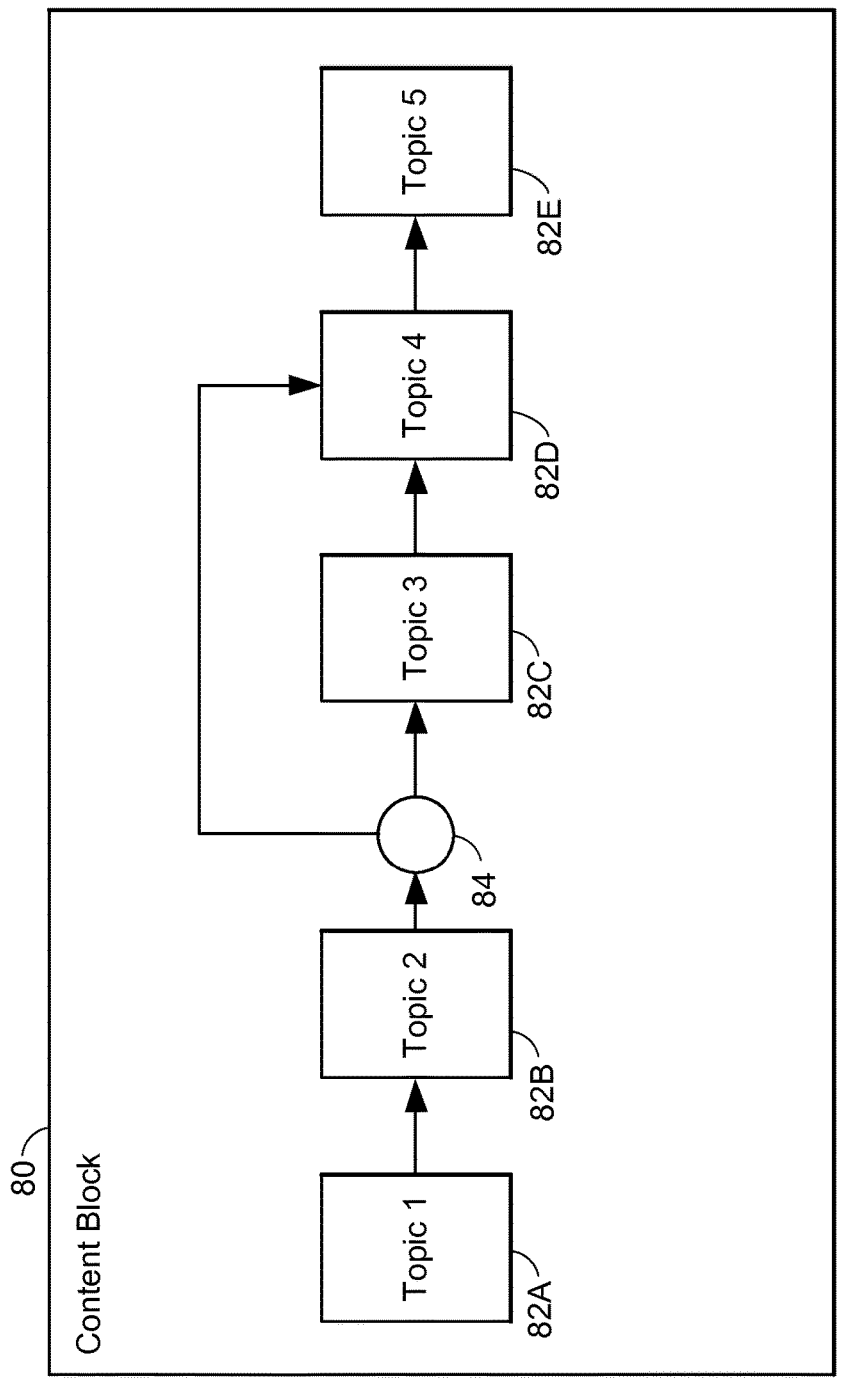
FIG. 5 depicts an example content block (e.g., within a program), according to an embodiment.

FIG. 5 depicts an example content block 80, which may correspond to one of the content blocks 74 of program 70 in FIG. 4, or a content block within a different program, for instance. The content block 80 includes five topics 82A-82E, and one decision point 84. As seen in FIG. 5, topics 82A, 82B, 82D and 82E are activated for each and every presentation/instance (so long as the content block 80 is completed from beginning to end), whereas topic 82C is only conditionally activated depending on the results of the evaluation at decision point 84.

Figure 6:
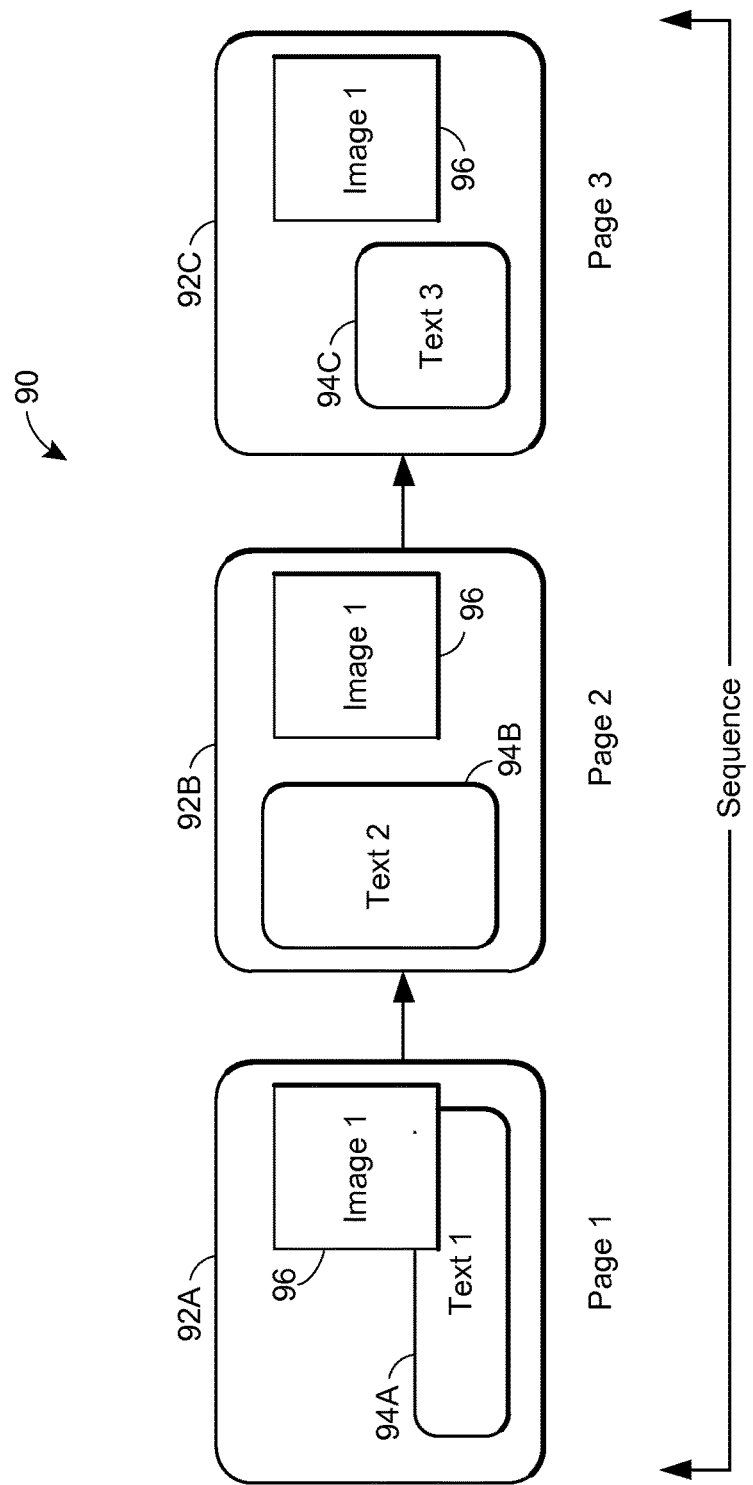
FIG. 6 depicts an example sequence (e.g., within a content block), according to an embodiment.

FIG. 6 depicts an example sequence 90, which may correspond to a particular sequence within one of the topics 82, or a sequence within a different topic, for instance. The sequence 90 includes three pages 92A-92C. As seen in FIG. 6, each of the pages 92 includes some text 94 and an image 96. The text 94 and image 96 may be viewed as elements within the element layer 32 of hierarchy 10 in FIG. 1, for example. Whereas the text changes from text 94A in page 92A, to text 94B in page 92B, to text 94C in page 92C, however, the image 96 remains fixed within each of the pages 92. In other embodiments, each of the pages 92 may include or be associated with more, fewer and/or different types of content than are shown in FIG. 6 (e.g., animated graphics, video, audio, etc.). Moreover, in some other embodiments, the flow of pages within a particular sequence may be dynamic (e.g., the sequence 90 may include one or more decision points between the pages 92 and/or other pages not shown in FIG. 6).

III. Example Use Cases

Several example use cases for an IMP, or a portion of an IMP, will now be described in connection with FIGS. 7-11. While these use cases assume a hierarchy similar to hierarchy 10 of FIG. 1, it is understood that similar approaches may be developed using other hierarchical arrangements. More generally, the examples of FIGS. 7-11 correspond to just a few of a virtually limitless possibilities for an IMP design.

Figure 7:
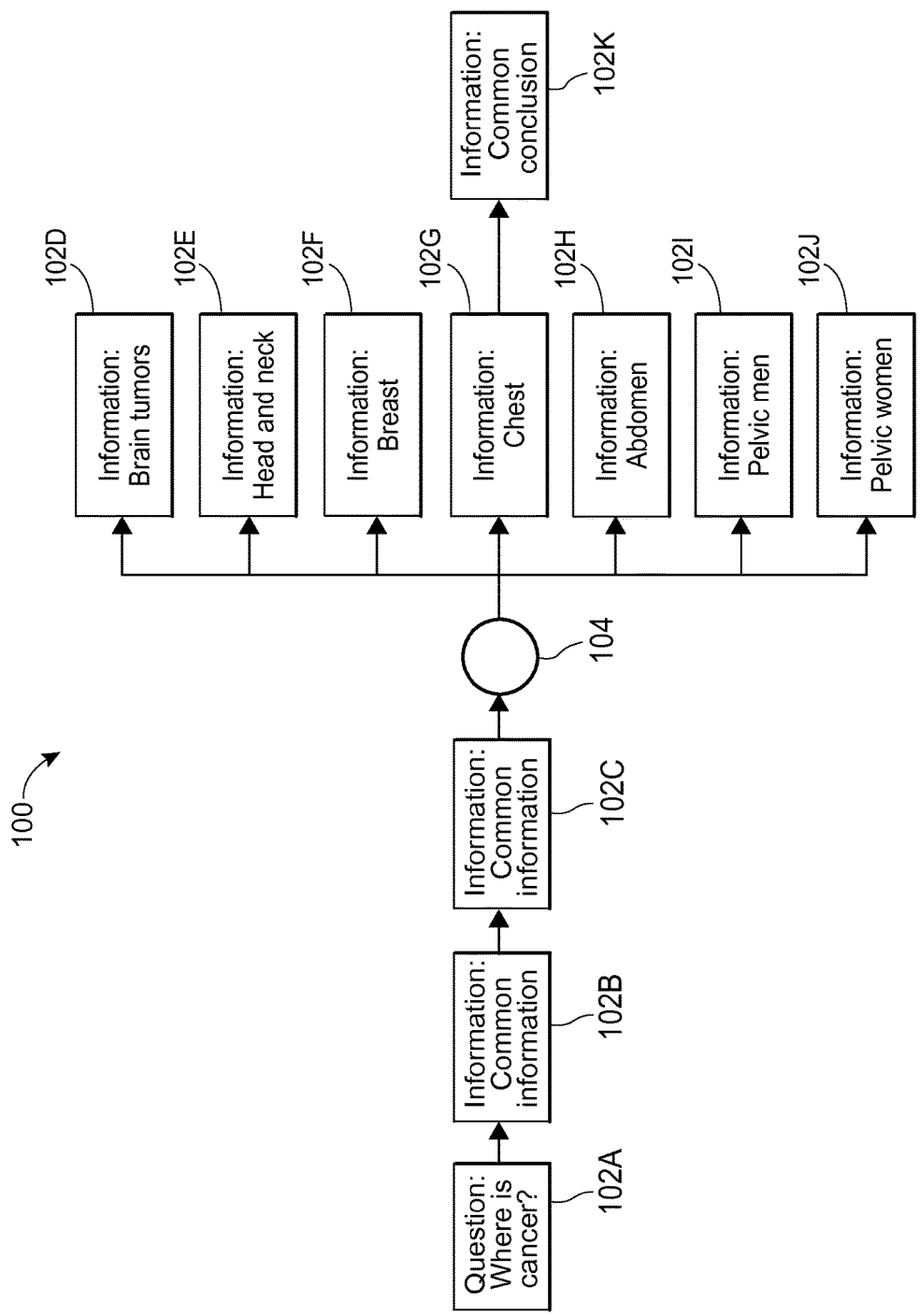
FIG. 7 depicts an example radiation therapy program, according to an embodiment.

Referring first to FIG. 7, a radiation therapy program 100 includes a number of nodes 102A-102K and a single decision point 104. With reference to the hierarchy 10 of FIG. 1, the nodes 102 may be different content blocks within content block layer 20 or different topics within topic layer 22, for example. As seen in FIG. 7, each of nodes 102A and 102B prompts a patient using the radiation therapy program 100 to answer a question. The prompts may provide an indication of the mechanism by which the patient should respond. If the question is presented as text, for example, a blank field for the answer may be shown adjacent to that text. In other embodiments, the mechanism for responding is not necessarily indicated by the presentation of the question, but is consistent throughout the radiation therapy program 100. For example, the patient may respond to any or all questions in the radiation therapy program 100 by speaking the response into a microphone of the patient's device.

Each of nodes 102C-102K presents different information to the patient (e.g., via text, audio, video, etc.). Whereas the information at nodes 102C and 102K may be presented to all patients during all presentations of the program 100, the information in only one of nodes 102D-102J is presented to a particular patient during a specific presentation of the program 100. The rules engine may decide which of nodes 102D-102J to activate at decision point 104 by firing a rule that operates on the facts obtained from the patient at nodes 102A and 102B (i.e., where the patient's cancer is located and whether the patient is male or female), for example. In some embodiments, nodes 102A and 102B are only activated if the information requested at those nodes is not already known. In such an embodiment, another decision point may be located prior to node 102A, with a first branch from the decision point (corresponding to the information being included in available records) leading directly to node 102C, and a second branch from the decision point (corresponding to the information not being included in available records) leading directly to node 102A.

Figure 8:
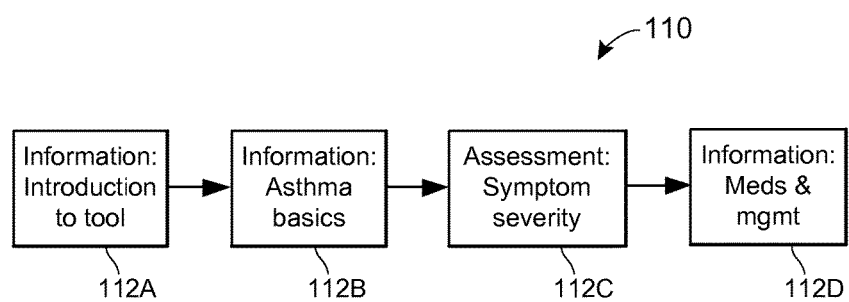
FIG. 8 depicts an example asthma medication decision support program, according to an embodiment.

Referring next to FIG. 8, an asthma medication decision support program 110 includes a number of nodes 112A-112E, without any decision points. With reference to the hierarchy 10 of FIG. 1, the nodes 112 may be different content blocks within content block layer 20, for example. As seen in FIG. 8, nodes 112A and 112B may provide background information to the patient who is using the program 110. Thereafter, at node 112C the patient may be prompted to assess the severity of his or her asthma-related symptoms. At node 112D, the patient may be provided information specifically directed to asthma medications and management. The specific type of information presented at node 112D may be selected for presentation based upon the patient's assessment at node 112C, for example. In some embodiments, information that the patient entered at node 112C may be sent to healthcare professionals (e.g., staff for the patient's doctor) at node 112D, at an earlier node, or at another node not shown in FIG. 8.

Figure 9:
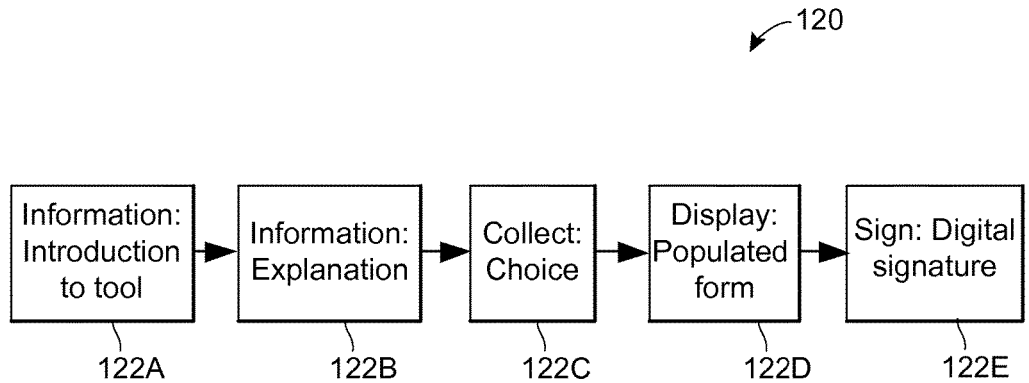
FIG. 9 depicts an example advance directive program, according to an embodiment.

Referring next to FIG. 9, an advance directive program 120 includes a number of nodes 122A-122E. With reference to the hierarchy 10 of FIG. 1, the nodes 122 may be different content blocks within content block layer 20, for example. As seen in FIG. 9, node 122A may provide background information to the patient who is using the program 120, and node 122B may provide an explanation of a particular type of advance directive choice to be made by the patient. Thereafter, at node 122C, the patient may be prompted to make the choice corresponding to that explanation. While such an arrangement is not shown in FIG. 9, nodes 122B and 122C may be repeated for all advance directive choices that the patient needs to make. The choice made at node 122C (or the choices made at the multiple iterations of node 122C) may then be used to auto-populate an advance directive form, and the populated form may be displayed to the patient at node 122D. The patient may then be prompted to digitally sign the form at node 122E.

Figure 10:
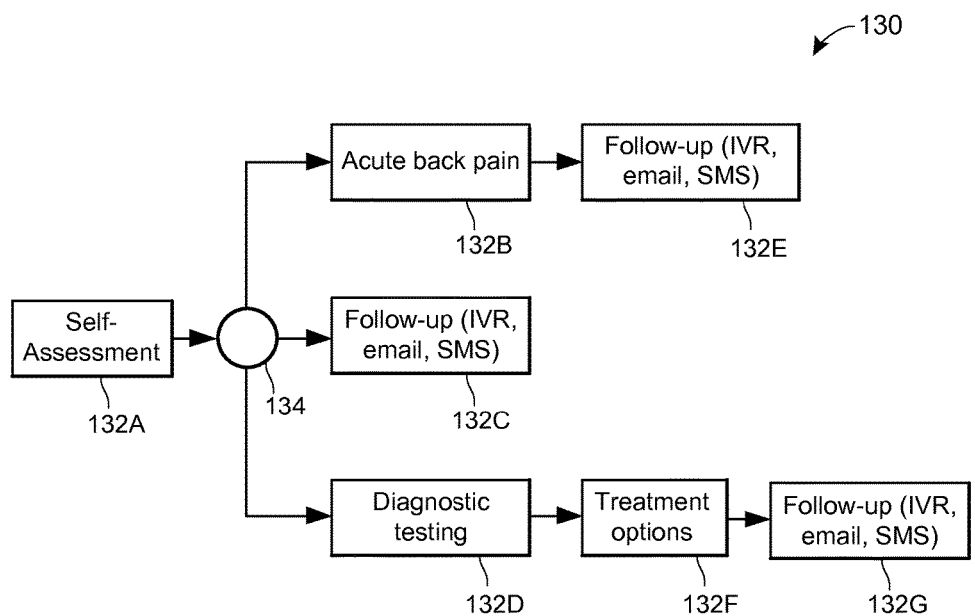
FIG. 10 depicts an example back pain decision support IMP, according to an embodiment.

Referring next to FIG. 10, a back pain decision support IMP 130 includes a number of nodes 132A-132G and a decision point 134. With reference to the hierarchy 10 of FIG. 1, the nodes 132 may be different programs within program layer 14, or different content blocks within the content block layer 20, for example. As seen in FIG. 10, at node 132A the patient using the IMP 130 may be prompted to provide a self-assessment (e.g., for severity of symptoms). Thereafter, it may be evaluated at decision point 134 whether to activate the path with nodes 132B and 132E, the path with node 132C, or the path with nodes 132D, 132F and 132G. The rules engine may make this decision by applying the information obtained from the self-assessment at node 132A to the appropriate rule(s).

Figure 11:
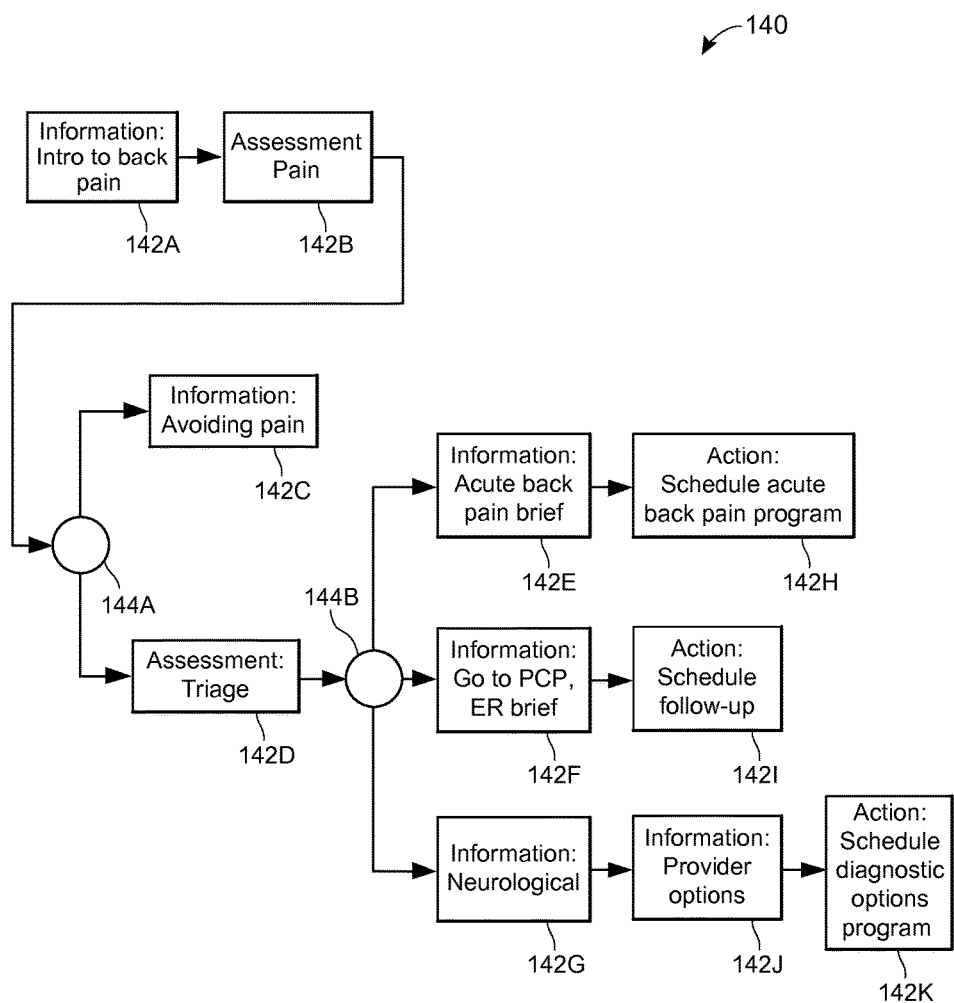
FIG. 11 depicts an example program within the back pain decision support IMP of FIG. 10, according to an embodiment.

Referring last to FIG. 11, a back pain decision support program 140 includes a number of nodes 142A-142K, with two decision points 144A and 144B. With reference to the hierarchy 10 of FIG. 1, the nodes 142 may be different content blocks within the content block layer 20. In one embodiment where the nodes 132 of FIG. 10 are programs, for example, the program 140 may correspond to the node 132A. As seen in FIG. 11, node 142A may provide background information about back pain, and node 142B may prompt the patient to perform a first portion of the self-assessment. The rules engine may apply answers/information that the patient provided during the first portion of the self-assessment (and/or other information derived therefrom) to the applicable rule(s) to determine whether to forego additional self-assessment and provide information about how to avoid back pain (at node 142C), or to instead continue on with a second portion of the self-assessment at node 142D.

If node 142D has been activated and the second portion of the self-assessment has been completed by the patient, the rules engine may apply answers/information that the patient provided during the second portion of the self-assessment (and/or other information derived therefrom) to one or more additional rules to determine whether to forego additional self-assessment and provide information about acute back pain (at node 142E) or information about visiting the patient's primary care physician or the emergency room (at node 142F), or to instead continue on with a third portion of the self-assessment (at node 142G). If the patient is presented with, and completes, the third portion of the self-assessment at node 142G, the information gathered from the patient at node 142G (and/or other information derived therefrom) may be used by a back-end server to determine provider options, which may be displayed or otherwise presented to the patient at node 142J. Finally, appropriate actions may be taken at node 142H, 142I or 142K (e.g., by a back-end server), depending on which decision was made at decision point 144B. For example, another program may be scheduled for the patient at node 142H or 142K, or a follow-up doctor appointment may be scheduled for the patient at node 142I.

IV. Example System

Figure 12:
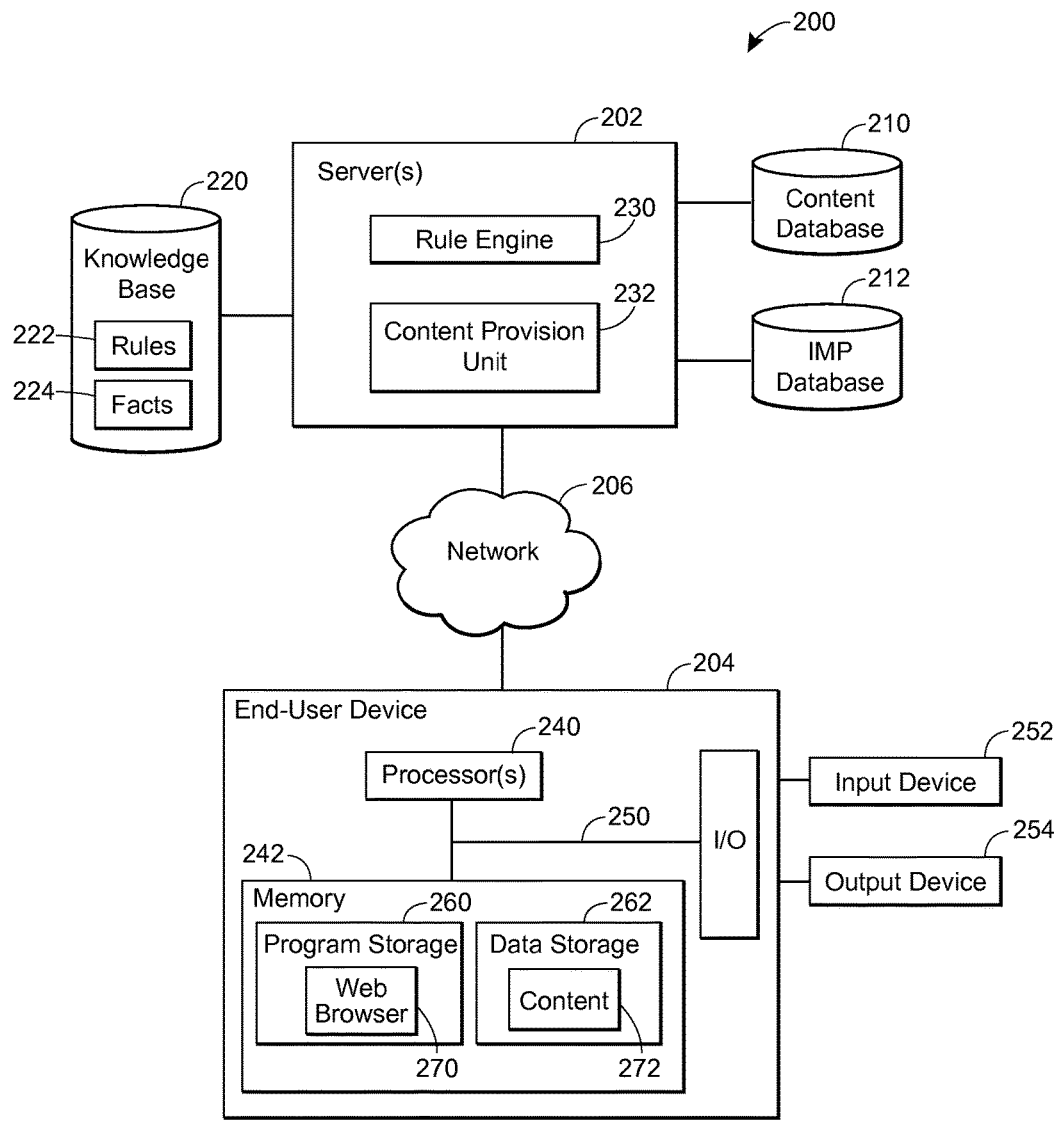
FIG. 12 is a block diagram of an example system for providing an IMP to an end-user, according to an embodiment.

FIG. 12 is a block diagram of an example system 200 for providing an IMP to a patient or other end-user. In the example embodiment of FIG. 12, the system 200 includes one or more servers 202 and an end-user device 204, which may be communicatively coupled to each other (directly or indirectly) via a network 206. The network 206 may be any suitable network or collection of networks, and may include one or more wireless and/or one or more wired links (e.g., including the Internet). While FIG. 12 shows only the single end-user device 204, many different devices of many different end-users may be coupled to the server(s) 202 (e.g., also via network 206).

The server(s) 202 may include or be coupled to a content database 210 storing multimedia content assets, such as audio content, image content, video content, and/or text content, for example. File formats for the content assets may be of any suitable format(s), such as PNG, GIF, JPEG and/or SVG files for graphics, MP4, MP2, MOV and/or F4V files for video, XML, PDF and/or HTML files for text, and MP3, OGG and/or WAV files for audio, for example. In some embodiments, the content assets stored in the content database 220 are managed by a content management system (CMS) that permits assets to be reused between different IMPs and/or between different portions within a single IMP.

The server(s) 202 may also include or be coupled to an IMP database 212 storing instructions corresponding to the respective nodes of one or more IMPs. The IMP database 212 may store HTML5 instructions that specify, for each node, the content asset(s) that is/are to be presented, as well as the presentation of that content. For example, the HTML5 instructions may specify the layout(s), font(s), and/or one or more other characteristics for each content asset within each presented page/screen within a given node.

The server(s) 202 may also include or be coupled to a knowledge base 220 including one or more databases that store rules 222 and facts 224. Each of facts 224 may generally be a variable or attribute value. As just a couple examples, one of the facts 224 may indicate the existence of various diseases or disorders (e.g., diabetes, heart disease, cancer, etc.) or identify demographic information for a person (e.g., gender, blood type, height, weight, age, etc.). The facts 224 may include facts based on information provided by the end-user during presentation of an IMP, and/or facts based on information obtained from other data sources (e.g., any of the data sources discussed below in connection with Section V).

Each of rules 222 may generally specify a condition and an action. When a particular rule is evaluated, one or more of facts 224 may be used to determine whether the condition specified by the rule is true. If the condition is true, the corresponding action may be initiated. The action may specify a node or collection of nodes to activate, for example. To provide a more specific example, a particular rule may specify the condition of a person being a smoker, evaluate that condition by using the fact that the person smokes (e.g., based on earlier input from the end-user), and initiate a "stop smoking" program in response to the condition being evaluated as true. In some instances, the action may specify a new fact to insert into the facts 222 in knowledge base 220. For example, if a needed fact does not exist in knowledge base 220 or has not been defined, an input prompt may be activated to request user input that can be used to define a new fact.

The server(s) 202 may include a rules engine 230 and a content provision unit 232. In some embodiments, one or both of the rules engine 230 and the content provision unit 232 may be components of software stored on computer-readable media (e.g., a random access memory (RAM) and/or read-only memory (ROM) of the server(s) 202) and executed by one or more processors of the server(s) 202 to perform the functions described herein. Generally, the rules engine 230, when fired by server(s) 202, may evaluate rules 222 using facts 224, as discussed above, during run-time of a presentation (e.g., program) in order to determine which nodes of the presentation are to be activated and/or the order of activation, and the content provision unit 232 may determine the timing with which the corresponding content assets from content database 210 are sent to the end-user device 204. It is noted that, as used herein, a "node sequence" may generally refer to an ordered series of nodes at any hierarchy layer, and does not necessarily refer to nodes at a sequence layer such as sequence layer 24 of FIG. 1.

In an embodiment, one of server(s) 202 is a content server responsible for providing content assets from content database 210 to the end-user device 204, and a different server of server(s) 202 is a rules engine server responsible for implementing the rules engine 230. For example, the content server (e.g., including content provision unit 232) and/or the content database 212 may be associated with an IMP provider, and the rules engine 230 and/or the knowledge base 220 may be associated with a third party that provides a commercial rules engine. In other embodiments, the rules engine 230 and content provision unit 232 are implemented by the same server.

The end-user device 204 may be a tablet, smartphone, laptop, desktop, or any other mobile, portable or stationary computing device that is associated with the end-user (e.g., patient) and has wireless and/or wired communication capabilities. The end-user device 204 may include one or more processors 240 communicatively coupled to a memory 242 and an I/O interface 246 via a system bus 250. Moreover, the end-user device 204 may be coupled to one or more input devices 252 (e.g., a touchscreen, a keyboard, a mouse, and/or a microphone) and one or more output devices 254 (e.g., the touchscreen, a monitor, and/or a speaker) via the I/O interface 246. Generally, the I/O interface 246 may include one or more interfaces for sending and receiving data and/or instructions, such as a communication interface, a video interface, an input interface, etc.

The memory 242 may include one or more memory devices including computer-readable media, and may include volatile and/or non-volatile memory such as read-only memory (ROM) and/or random access memory (RAM), for example. In the embodiment of FIG. 12, the memory 242 includes a program storage 260 storing programs/instructions that may be executed by the processor(s) 240, and a data storage 262 storing data used by those programs when executed by the processor(s) 240. The programs stored in program storage 260 may include a web browser application 170. When executed by processor(s) 240, the web browser application 170 may provide an HTML5-capable web browser, for example.

In operation, the server(s) 202 may identify a presentation that is to be presented to the end-user (e.g., based on data indicating which presentation a doctor has "prescribed" to the end-user, data indicating which presentation the end-user has requested, data indicating the end-user's progress in a partially-completed presentation, etc.). The identified presentation may be any one of the IMPs or IMP portions that are shown in FIGS. 2-11, for example, or may be a different IMP or IMP portion.

The server(s) 202 may then fire the rules engine 230 for the identified presentation. Generally, as discussed above, the rules engine 230 may, as the end-user steps through the presentation, utilize the rules 222 and facts 224 to determine which node(s) is/are next to be activated. After the rules engine 230 has identified a particular next node or node sequence, the content provision unit 232 identifies the content assets associated with that node or node sequence, and causes those content assets to be sent to the end-user device 204. As described further below, the content provision unit 232 may generally attempt to provide content assets to the end-user device 204 in a manner that allows the end-user device 204 to seamlessly present the content assets of the successive activated nodes to the end-user, without long gaps/delays between nodes, and with little or no buffering at the end-user device 204. The content provision unit 232 may further cause the server(s) 202 to send to the end-user device 204, for each node associated with content assets, instructions specifying the presentation of those content assets (e.g., node-specific HTML5 instructions stored in database 212).

At the end-user device 204, the content assets provided by content provision unit 232 may be assembled substantially in real-time as those content assets are received (or, in some embodiments and/or scenarios, as the end-user device 204 requests those content assets), and seamlessly presented to the end-user in the order determined by the rules engine 230 according to the corresponding instructions (e.g., HTML5 instructions). The content assets may be presented in a graphical user interface (GUI) via web browser application 270 and output device(s) 254, for example. The processor(s) 240 may implement a secure platform for presenting content to, or receiving information from, the end-user, in order to ensure compliance with HIPAA and/or other data security standards.

Because communication link (e.g., Internet) speeds are finite, the content assets may be buffered in data storage 262 as content 272. However, the end-user device 204 may begin to present portions of received content assets to the end-user before an entirety of the content assets are received or buffered. If the end-user device 204 is receiving a video content asset, for example, the end-user device 204 may begin playing that video for the end-user before the entire video has been received.

To help ensure that content is provided in a manner that allows seamless (or nearly seamless) presentation at the end-user device 204, with limited or no impact from the buffering in data storage 262, the processor(s) 240 may implement a multi-thread process. In the multi-thread process, one thread may be responsible for obtaining/producing content assets and presentation instructions (e.g., HTML5 instructions) associated with those content assets, while another thread may be responsible for consuming the obtained content assets according to the associated presentation instructions. The thread for obtaining/producing content assets may generate, and send to the server(s) 202, messages indicating when the end-user device 204 is ready for additional content. The messages may include explicit requests for additional content, for example, and/or requests that the server(s) 202 temporarily refrain from sending more content (e.g., for a predetermined time period, or until the end-user device 204 sends a next "ready for content" message, etc.).

The content provision unit 232 may detect the messages indicating when additional content should be sent, and in response cause a fixed or limited number or size of content assets (referred to herein as a "chunk" of content assets) for upcoming nodes to be sent to the end-user device 204. Alternatively, the content provision unit 232 may at that time cause content assets for upcoming nodes to be sent at a fixed or limited rate (e.g., such that a maximum average data rate is not exceeded, etc.), up until the content provision unit 232 detects that end-user device 204 has requested that server(s) 202 refrain from sending additional content.

In addition to determining when to send content assets, the content provision unit 232 may determine precisely which of the content assets in content database 210 should be sent within a next content chunk. To make this latter determination, the content provision unit 232 may, for example, communicate with the rules engine 230 to identify which node(s) of the presentation, if any, will next be activated (unconditionally), and add the content assets corresponding to as many of those nodes as possible to the content chunk (e.g., up to, but not exceeding, a predetermined chunk size). As another example, the content provision unit 232 may communicate with the rules engine 230 to identify not only a first node sequence that will unconditionally be activated next, but also alternative node sequences corresponding to different results at a decision point that immediately follows the first node sequence. If the maximum content chunk size (if any) allows it, content assets corresponding to at least some of the conditionally-activated nodes in the alternative node sequences may be sent to the end-user device 204.

Referring to FIG. 4, for example, the rules engine 230 may determine that nodes (content blocks) 74C and 74E will unconditionally be activated next, and that either nodes 74G, 74I or nodes 74H, 74I will conditionally be activated thereafter. Based on this knowledge, the content provision unit 232 may decide to send only content assets for nodes 74C, 74E before waiting for a next request for additional content, or may decide to send content assets for nodes 74C, 74E, 74G, 74H (or 74C, 74E, 74G, 74H, 74I, etc.), for example. By including content assets for nodes beyond an upcoming decision point, the content provision unit 232 may reduce the likelihood that the end-user experiences delays between nodes.

In some embodiments, the system 200 may include additional, fewer and/or different components than are shown in FIG. 12, and/or the components shown in FIG. 12 are arranged in a different manner. In one alternative embodiment, for example, the rules engine 230 may be stored and/or implemented at the end-user device 204. Moreover, in some embodiments, other functionality or data provided by the system 200 may be provided by or at the end-user device 204 (e.g., the memory 242 may store the content database 210, the IMP database 212, and/or the knowledge base 220).

In some embodiments and/or scenarios, the end-user device 204 may be capable of receiving and presenting different IMP portions (e.g., programs) via one or more additional communication channels. For instance, the end-user device 204 may be a smartphone and, in addition to presenting IMP portions with multimedia content as described above, may include call capabilities allowing portions of the IMP to be presented to the end-user via IVR, and/or texting capabilities allowing portions of the IMP to be presented to the end-user via SMS text messages. Alternatively, or additionally, the end-user may use one or more other devices, in addition to end-user device 204, to access different portions of the IMP. For instance, the end-user device 204 may be a tablet device, and the end-user may also have a landline phone via which IVR editions of various portions of the IMP may be presented to the end-user, and/or a mobile phone via which SMS text message editions (and/or IVR editions) of various portions of the IMP may be presented to the end-user.

V. Example Data Sources

The facts operated upon by the rules of the rules engine (e.g., facts 224 of FIG. 12) may be generated or updated using any one or more of various different data sources, in different embodiments. For instance, some facts may be added to, or updated in, a knowledge base (e.g., knowledge base 220 of FIG. 12) by analyzing information provided by the end-user. As a more specific example, a fact relating to pain severity level may be set to a value between 1 and 10 based on a value that was entered by the end-user when prompted to rate his or her pain level on a scale of 1 to 10. In some embodiments and/or scenarios, facts may be derived from, but different than, information entered by the end-user. For example, a knowledge base may store the fact "pain=high" if the end-user entered a pain level value between 6 and 10, or the fact "pain=low" if the end-user entered a pain level value between 1 and 5.

In other embodiments and/or scenarios, other data sources may also be used to add facts to the knowledge base, and/or to update facts already existing in the knowledge base. For example, facts may be added or updated using data from electronic medical record (EMR) software or systems (e.g., for facts relating to patient encounter and/or diagnosis data), data from customer and/or partner relation management (CRM or PRM) software or systems (e.g., for facts relating to when a patient was contacted, and why), data from analytics vendors, software or systems (e.g., for facts relating to patient populations/cohorts), data from patient registry software or systems (e.g., for facts relating to patient scheduling), and/or data from prescription software or systems (e.g., for facts relating to whether a patient has, or has filled, a particular prescription). As another example, facts may be added or updated using data from personal and/or bedside biometric or other medical devices. For instance, one or more facts relating to the vital signs of a patient may be periodically updated based on signals from a heart monitor worn by the patient.

The data from these other sources may be obtained in any suitable manner. For example, server(s) 202 of FIG. 12 may request the data from one or more third party servers via network 206. As another example, a biometric device worn by the patient may use a Bluetooth link to transfer biometric data to the patient's smartphone, and an application executing on the patient's smartphone may transmit the data to the server(s) 202 via network 206.

VI. Example Method

Figure 13:
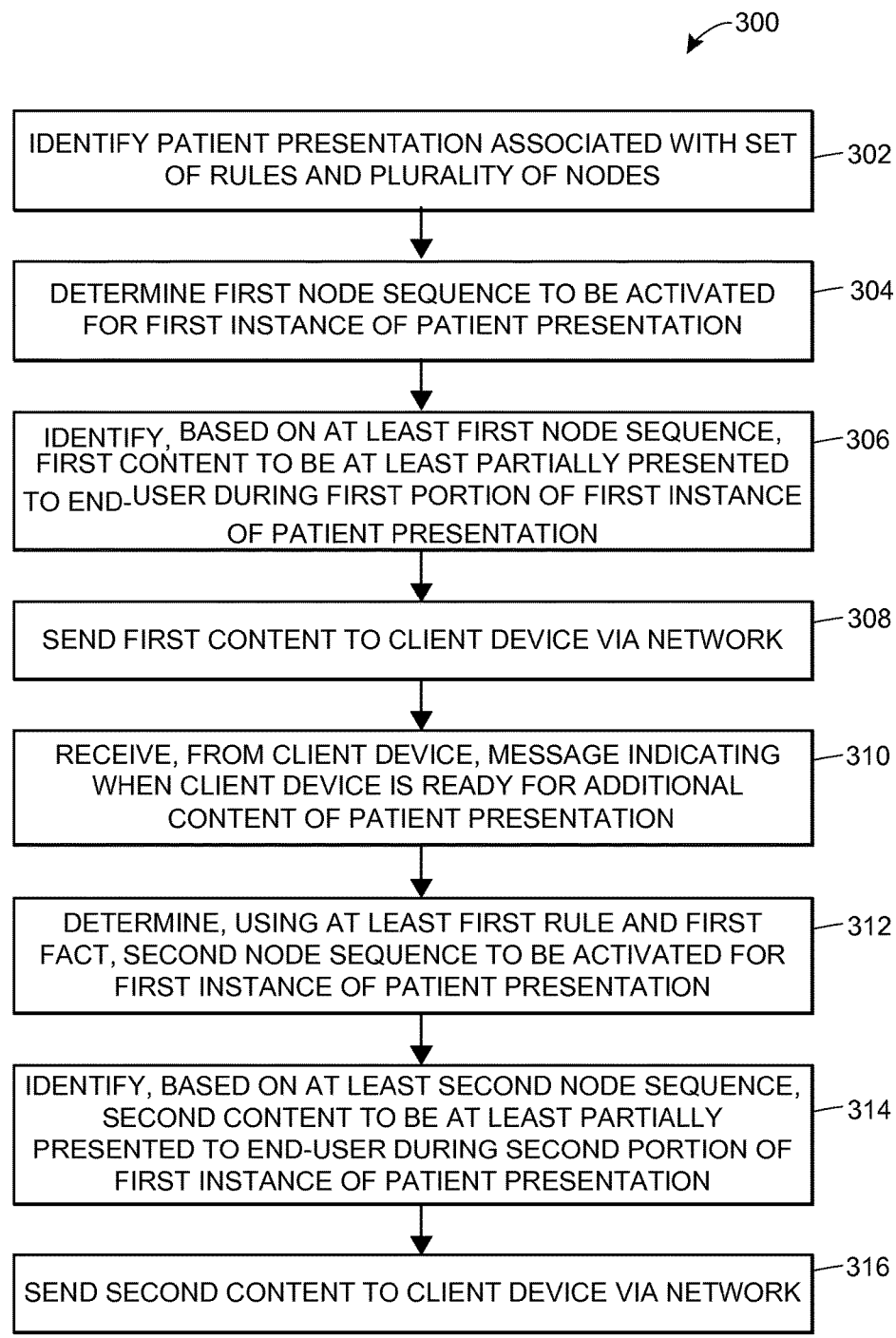
FIG. 13 is a flow diagram of an example method for seamlessly providing health-related information to a patient or other end-user, according to an embodiment.

FIG. 13 is a flow diagram of an example method 300 for seamlessly providing health-related information to a patient or other end-user, according to an embodiment. The method 300 may be implemented by one or more servers, such as server(s) 202 of FIG. 12 (e.g., one or more processors of server(s) 202, when executing instructions stored in one or more memories of server(s) 202), for example.

In the example method 300, a patient presentation is identified for the end-user (block 302). The patient presentation may be an IMP or a portion of an IMP. With reference to the layers of hierarchy 10 discussed in connection with FIG. 1, for example, the patient presentation may be an IMP, a program, a content block, a topic, or a different layer of hierarchy 10. The patient presentation may be associated with a set of rules and a plurality of nodes (e.g., content blocks if the patient presentation is a program, topics if the patient presentation is a content block, etc.). For any particular instance/occurrence of the patient presentation (e.g., each time the presentation is restarted for a new user), each of at least some of the plurality of nodes may be selectively activated, or selectively not activated, in accordance with the set of rules when operating upon a set of facts. Moreover, each such node may correspond to one or more respective content assets that are to be presented to the end-user if and only if that node is activated. The content assets may include text, audio, video, images, etc., or a combination of two or more different content types (e.g., text, video and audio, etc.).

Other nodes of the plurality of nodes may be unconditionally activated for each instance of the patient presentation. Still other nodes may not correspond to any content assets. For example, the plurality of nodes may include one or more decision point nodes at which decisions to activate or not activate other nodes are made, and/or one or more nodes at which particular actions are taken (e.g., sending results to healthcare professionals) but no content is presented, etc.

Next, a first node sequence that is to be activated for a first instance of the patient presentation is determined (block 304), e.g., by a rules engine such as rules engine 230 of FIG. 12. The "first instance" may correspond to the first time that the end-user views/executes the patient presentation after being prescribed, or after requesting, the patient presentation, for example. The first node sequence may include a first subset of the plurality of nodes, and may be determined according to the set of rules (e.g., by evaluating a condition at a decision point just prior to the first node sequence, or by applying a default rule under which all nodes not preceded by a decision point are automatically activated, etc.).

Also in the method 300, first content is identified based on at least the first node sequence (block 306). The first content may be content that is to be at least partially presented to the end-user during a first portion of the first instance of the patient presentation, and may include the respective content assets that correspond to the first subset of the plurality of nodes. Generally, in some embodiments, content may be identified at block 306 according to one or more algorithms or criteria. For example, the goal may be to identify a collection of content assets that includes the content assets associated with as many nodes of the first node sequence as possible, subject to one or more restrictions (e.g., a maximum byte size for the identified content).

After being identified, the first content is sent to a client device (block 308), where the first content may be assembled substantially in real-time as the first content is received (or, alternatively, as the end-user or client device requests the first content). The client device may be a device associated with the end-user, such as end-user device 204 of FIG. 12, and/or the first content may be sent via a network similar to network 206 of FIG. 12, for example. In some embodiments, the first content is sent along with first HTML5 instructions including instructions specifying the structure and presentation of the first content at the client device (e.g., instructions specifying the layout(s) used to present the first content, etc.).

After the first content is sent to the client device at block 308, a message is received from the client device (block 310). The message may indicate when the client device is ready for additional content of the patient presentation. For example, the message may be an explicit request for more content, or a different message from which the appropriate time to send additional content can be inferred (e.g., a "hold content" message, where it is known a priori that content is only to be withheld for a predetermined time interval after such a message is received, or a message specifying precisely when additional content should be provided, etc.). The client device may have generated and sent the message for various different reasons, in different embodiments. For example, the client device may have recognized that it had already presented most of the first content, and/or that a link to a server implementing the method 300 was no longer impaired, etc.

A second node sequence that is to be activated for the first instance of the patient presentation is determined using at least a first rule of the set of rules and a first fact of the set of facts (block 312), e.g., as implemented by a rules engine such as rules engine 230 of FIG. 12. The second node sequence may include a second subset of the plurality of nodes. The first fact may be a fact that was generated or updated by the server(s) implementing the method 300 in accordance with an input made by the end-user. For example, the first subset of the plurality of nodes in the first node sequence may have included a node that, when activated, caused the client device to present a user prompt to the end-user, and the method 300 may have included an additional block (not shown in FIG. 13) in which data indicative of the responsive input is received from the client device. Alternatively, the first fact may be a fact from a different source, such as any of the other data sources discussed above in Section V, for example.

Also in the method 300, second content is identified based on at least the second node sequence (block 314). The second content may be content that is to be at least partially presented to the end-user during a second portion of the first instance of the patient presentation, and may include at least a portion of the respective content assets that correspond to the second subset of the plurality of nodes. The second content may be identified according to the same algorithms or criteria by which the first content was identified, for example.

After being identified, the second content is sent to the client device via the network (block 316). In some embodiments, the second content is sent along with second HTML5 instructions, including instructions specifying the structure and presentation of the second content at the client device (e.g., instructions specifying the layout(s) used to present the second content, etc.).

In some embodiments, some of the blocks of the method 300 are not performed in the order shown in FIG. 13. In one embodiment and/or scenario, for example, determining the second node sequence at block 312 is performed partially or entirely before receiving the message at block 310. Moreover, in some embodiments, different ones of the blocks of the method 300 are performed by different servers. For example, a rules engine server may perform at least blocks 304 and 312, while a different, content server may perform at least blocks 306, 308, 310, 314 and 316.

Two specific examples, corresponding to variations of the embodiment of method 300, will now be provided with reference to FIG. 4 for illustrative purposes. It is understood, however, that these are just two of many possible variations of the embodiment of method 300. Both embodiments are described in the context of a specific scenario in which it is determined, at decision point 76A, to activate node 74C rather than node 74B.

In the first embodiment, the program 70 of FIG. 4 is identified as a patient presentation for the end-user at block 302. At block 304, the first node sequence is determined to include node (content block) 74A. At block 306, the first content is identified such that it includes only the content asset(s) associated with node 74A. At block 312, the second node sequence is determined to include node 74C, and possibly node 74E (which unconditionally follows node 74C). At block 314, the second content is identified such that it includes the content asset(s) associated with node 74C, and possibly the content asset(s) associated with node 74E.

In the second embodiment, as in the first embodiment, the program 70 is identified as a patient presentation for the end-user at block 302, and the first node sequence is determined to include node 74A at block 304. In the second embodiment, however, the first content identified at block 306 includes not only the content asset(s) associated with node 74A, but also the content assets associated with at least nodes 74B and 74C. While this approach may cause some unused content to be delivered to the client device, it may ensure that at least some content will be immediately available for presentation just after the decision point 76A, without significant delay, regardless of the result of the evaluation at decision point 76A. At block 312, as in the first embodiment, the second node sequence is determined to include node 74C, and possibly node 74E. Because the first content sent at block 308 in the second embodiment had already included the content asset(s) associated with node 74C, however, the second content identified at block 314 includes the content asset(s) of node 74E but omits the content asset(s) of node 74C. Moreover, in the second embodiment, in order to once again ensure that at least some content will be immediately available just after the decision point (here, decision point 76B) regardless of the result of the corresponding evaluation, the second content may further include at least the content assets associated with nodes 74G and 74H.

VII. Exemplary Aspects of the Invention

In some embodiments, the invention includes at least one of the aspects enumerated below:

1. A method for seamlessly providing health-related information to an end-user, the method comprising:

identifying, at one or more servers, a patient presentation for the end-user, the patient presentation being associated with (i) a set of rules and (ii) a plurality of nodes, wherein each of at least some of the plurality of nodes is selectively activated, or selectively not activated, for a particular instance of the patient presentation in accordance with the set of rules when operating upon a set of facts, and corresponds to one or more respective content assets that are to be presented to the end-user if and only if the node is activated;

determining, at the one or more servers, a first node sequence to be activated for a first instance of the patient presentation, the first node sequence including a first subset of the plurality of nodes;

identifying, at the one or more servers and based on at least the first node sequence, first content that is to be at least partially presented to the end-user during a first portion of the first instance of the patient presentation, the first content including the respective content assets that correspond to the first subset of the plurality of nodes;

sending, from the one or more servers, the first content to a client device via a network;

receiving, at the one or more servers and from the client device, a message indicating when the client device is ready for additional content of the patient presentation;

determining, at the one or more servers and using at least (i) a first rule of the set of rules and (ii) a first fact of the set of facts, a second node sequence to be activated for the first instance of the patient presentation, the second node sequence including a second subset of the plurality of nodes;

identifying, at the one or more servers and based on at least the second node sequence, second content that is to be at least partially presented to the end-user during a second portion of the first instance of the patient presentation, the second content including at least a portion of the respective content assets that correspond to the second subset of the plurality of nodes; and sending, from the one or more servers and after receiving the message, the second content to the client device via the network.

2. The method of aspect 1, wherein:

identifying first content that is to be at least partially presented to the end-user includes identifying first content that includes (i) the respective content assets that correspond to the first subset of the plurality of nodes, (ii) the respective content asset or assets that correspond to at least a starting node of the second node sequence, and (iii) the respective content asset or assets that correspond to at least a starting node of a third node sequence;

determining a second node sequence to be activated for the first instance of the patient presentation includes determining that the third node sequence is not to be activated for the first instance of the patient presentation; and identifying second content that is to be at least partially presented to the end-user includes identifying second content that (i) includes a portion of the respective content assets that correspond to the second subset of the plurality of nodes, but (ii) omits at least the respective content asset or assets that correspond to the starting node of the second node sequence.

3. The method of aspect 2, wherein:

determining a first node sequence to be activated for a first instance of the patient presentation includes determining a first node sequence that ends at a decision point at which one or more conditions are evaluated, the starting node of the second node sequence corresponding to an evaluation of the one or more conditions producing a first result and the starting node of the third node sequence corresponding to the evaluation of the one or more conditions producing a second result.

4. The method of any one of aspects 1 through 3, wherein:

sending the first content to the client device further includes sending first HTML5 instructions to the client device, the first HTML5 instructions including instructions for presenting the first content at the client device; and sending the second content to the client device further includes sending second HTML5 instructions to the client device, the second HTML5 instructions including instructions for presenting the second content at the client device.

5. The method of any one of aspects 1 through 4, wherein:

determining a first node sequence to be activated for a first instance of the patient presentation includes determining the first node sequence at a rules engine server of the one or more servers;

identifying first content that is to be at least partially presented to the end-user includes identifying the first content at a content server of the one or more servers, the content server being a different one of the one or more servers than the rules engine server;

sending the first content to the client device includes sending the first content from the content server to the client device;

receiving a message indicating when the client device is ready for additional content includes receiving the message at the content server;

determining a second node sequence to be activated for the first instance of the patient presentation includes determining the second node sequence at the rules engine server;

identifying second content that is to be at least partially presented to the end-user includes identifying the second content at the content server; and sending the second content to the client device includes sending the second content from the content server to the client device.

6. The method of any one of aspects 1 through 5, wherein the first subset of the plurality of nodes includes a node that, when activated, causes the client device to present a user prompt to the end-user, and wherein the method further comprises:

receiving, at the one or more servers from the client device, first data indicative of an input made by the end-user at the client device in response to the user prompt; and prior to determining the second node sequence, defining, by the one or more servers, at least the first fact according to the input made by the end-user.

7. The method any one of aspects 1 through 6, wherein determining the second node sequence to be activated for the first instance of the patient presentation is performed by the one or more servers prior to receiving the message indicating when the client device is ready for additional content.

8. The method of any one of aspects 1 through 7, wherein one or both of:

identifying first content includes identifying first content that includes a first set of visual and audio elements; and identifying second content includes identifying second content that includes a second set of visual and audio elements.

9. The method of any one of aspects 1 through 8, wherein sending the first content to a client device includes sending the first content to a mobile device.

10. A system for seamlessly providing health-related information to an end-user, the system comprising:

one or more processors;

one or more memories storing instructions that, when executed by the one or more processors, cause the one or more processors to identify a patient presentation for the end-user, the patient presentation being associated with (i) a set of rules and (ii) a plurality of nodes, wherein each of at least some of the plurality of nodes is selectively activated, or selectively not activated, for a particular instance of the patient presentation in accordance with the set of rules when operating upon a set of facts, and corresponds to one or more respective content assets that are to be presented to the end-user if and only if the node is activated, determine a first node sequence to be activated for a first instance of the patient presentation, the first node sequence including a first subset of the plurality of nodes, identify, based on at least the first node sequence, first content that is to be at least partially presented to the end-user during a first portion of the first instance of the patient presentation, the first content including the respective content assets that correspond to the first subset of the plurality of nodes, send the first content to a client device via a network, receive from the client device a message indicating that the client device is ready for additional content of the patient presentation, determine, using at least (i) a first rule of the set of rules and (ii) a first fact of the set of facts, a second node sequence to be activated for the first instance of the patient presentation, the second node sequence including a second subset of the plurality of nodes, identify, based on at least the second node sequence, second content that is to be at least partially presented to the end-user during a second portion of the first instance of the patient presentation, the second content including at least a portion of the respective content assets that correspond to the second subset of the plurality of nodes, and send the second content to the client device via the network.

11. The system of aspect 10, wherein:

the identified first content includes (i) the respective content assets that correspond to the first subset of the plurality of nodes, (ii) the respective content asset or assets that correspond to at least a starting node of the second node sequence, and (iii) the respective content asset or assets that correspond to at least a starting node of a third node sequence;

the instructions cause the one or more processors to, in addition to determining a second node sequence to be activated for the first instance of the patient presentation, determine that the third node sequence is not to be activated for the first instance of the patient presentation; and the identified second content (i) includes a portion of the respective content assets that correspond to the second subset of the plurality of nodes, but (ii) omits at least the respective content asset or assets that correspond to the starting node of the second node sequence.

12. The system of aspect 11, wherein:

the first node sequence ends at a decision point at which one or more conditions are evaluated;

the starting node of the second node sequence corresponds to an evaluation of the one or more conditions producing a first result; and the starting node of the third node sequence corresponding to the evaluation of the one or more conditions producing a second result.

13. The system of any one of aspects 10 through 12, wherein the instructions are configured to:

send first HTML5 instructions to the client device with the first content, the first HTML5 instructions including instructions for presenting the first content at the client device; and send second HTML5 instructions to the client device with the second content, the second HTML5 instructions including instructions for presenting the second content at the client device.

14. The system of any one of aspects 10 through 13, wherein:

the first subset of the plurality of nodes includes a node that, when activated, causes the client device to present a user prompt to the end-user; and the instructions further cause the one or more processors to receive, from the client device, first data indicative of an input made by the end-user at the client device in response to the user prompt, and prior to determining the second node sequence, define at least the first fact according to the input made by the end-user.

15. The system of any one of aspects 10 through 14, wherein one or both of:

the first content includes a first set of visual and audio elements; and the second content includes a second set of visual and audio elements.

16. A system comprising:

a client device associated with an end-user;

a first data storage storing a knowledge base that includes a set of rules and a set of facts both associated with a patient presentation;

a second data storage storing a plurality of content assets for a plurality of nodes associated with the patient presentation, wherein each of at least some of the plurality of nodes (i) is selectively activated, or selectively not activated, for a particular presentation of the patient presentation in accordance with the set of rules when operating upon the set of facts, and (ii) corresponds to one or more respective content assets, of the plurality of content assets, that are to be presented to the end-user if and only if the node is activated; and one or more servers configured to (i) determine a first node sequence to be activated for a first instance of the patient presentation, the first node sequence including a first subset of the plurality of nodes, (ii) identify, based on at least the first node sequence, first content that is to be at least partially presented to the end-user during a first portion of the first instance of the patient presentation, the first content including the respective content assets that correspond to the first subset of the plurality of nodes, and (iii) send the first content to the client device via a network, wherein the client device is configured to (i) assemble the first content during the first instance of the patient presentation, (ii) present at least a portion of the assembled first content to the end-user, and (iii) prior to an entirety of the portion of the first content being presented to the end-user, send the one or more servers a message indicating when the client device is ready for additional content of the patient presentation, wherein the one or more servers are further configured to, after receiving the message indicating when the client device is ready for additional content, (i) determine, using at least a first rule of the set of rules and a first fact of the set of facts, a second node sequence to be activated for the first instance of the patient presentation, the second node sequence including a second subset of the plurality of nodes, (ii) identify, based on at least the second node sequence, second content that is to be at least partially presented to the end-user during a second portion of the first instance of the patient presentation, the second content including at least a portion of the respective content assets that correspond to the second subset of the plurality of nodes, and (iii) send the second content to the client device via the network, and wherein the client device is further configured to (i) assemble the second content during the first instance of the patient presentation, and (ii) present at least a portion of the assembled second content to the end-user.

17. The system of aspect 16, wherein the client device is a mobile device having a display device, a speaker, and one or more input devices.

18. The system of aspect 16 or 17, wherein the client device is configured to present at least the portion of the first content, and at least the portion of the second content, to the end-user via an HTML5-capable web browser.

19. The system of any one of aspects 16 through 18, wherein the client device is configured to execute a multi-thread process, the multi-thread process including (i) a first thread for producing content, the first thread generating the message indicating when the client device is ready for additional content, and (ii) a second thread for consuming content, the second thread assembling the first content and the second content substantially in real-time as the first content and the second content, respectively, are received by the client device.

20. The system of any one of aspects 16 through 19, wherein the message indicating when the client device is ready for additional content includes either (i) a message requesting additional content, or (ii) a message causing the one or more servers to refrain from sending additional content for a predetermined time period.

VIII. Additional Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

A. Network(s)

As used herein, unless otherwise specified, the term "network" is a collection of nodes (e.g., devices or systems capable of sending, receiving and/or forwarding information) and links which are connected so as to enable telecommunication between the nodes.

Generally speaking, the term "node" (when used in reference to a network topology, and to be distinguished from the "nodes" discussed above in connection with FIGS. 1-13) refers to a connection point, redistribution point, or a communication endpoint. A node may be any device or system (e.g., a computer system) capable of sending, receiving and/or forwarding information. For example, end systems that originate and/or ultimately receive a message are nodes. Intermediary device that receive and forward the message are also generally considered to be "nodes."

A "link" is a pathway or medium connecting two or more nodes. A link may be a physical link and/or a logical link. A physical link is the interface and/or medium(s) over which information is transferred, and may be wired or wireless in nature. Examples of physicals links may include a cable with a conductor for transmission of electrical energy, a fiber optic connection for transmission of light, and/or a wireless electromagnetic signal that carries information via changes made to one or more properties of an electromagnetic wave(s).

A logical link between two or more nodes represents an abstraction of the underlying physical links and/or intermediary nodes connecting the two or more nodes. For example, two or more nodes may be logically coupled via a logical link. The logical link may be established via any combination of physical links and intermediary nodes (e.g., routers, switches, or other networking equipment).

A link is sometimes referred to as communication channel. In a wireless communication system a channel generally refers to a particular frequency or frequency band. A carrier signal (or carrier wave) is transmitted at the particular frequency or within the particular frequency band of the channel. In some instances, multiple signals may be transmitted over a single band/channel. For example, signals may sometimes be simultaneously transmitted over a single band/channel via different sub-bands or sub-channels. As another example, signals may sometimes be transmitted via the same band by allocating time slots over which respective transmitters and receivers use the band in question.

As already noted, a network is a collection of nodes and links. A network may include dedicated routers responsible for directing traffic between nodes, and, optionally, dedicated devices responsible for configuring and managing the network. Some or all of the nodes may be also adapted to function as routers in order to direct traffic sent between other network devices. Network devices may be interconnected in a wired or wireless manner, and network devices may have different routing and transfer capabilities. For example, dedicated routers may be capable of high volume transmissions while some nodes may be capable of sending and receiving relatively little traffic over the same period of time. Additionally, the connections between nodes on a network may have different throughput capabilities and different attenuation characteristics. A fiberoptic cable, for example, may be capable of providing a bandwidth several orders of magnitude higher than a wireless link because of the difference in the inherent physical limitations of the medium. A network may include networks or subnetworks, such as a local area network (LAN) or a wide area network (WAN).

B. Communication Interface(s)

Some of the devices and/or systems described herein include a "communication interface" (sometimes referred to as a "network interface"). A communication interface of a system enables the system to send information to other system and/or receive information from other systems. In some instances, a communication interface of a system may be utilized to establish a direct connection to another system. In some instances, a communication interface of a system enables the system to connect to a network (via a link).

To illustrate, a communication interface can include circuitry for permitting wireless communication (e.g., short-range and/or long-range communication) with one or more devices or systems using any suitable communications protocol. For example, a communication interface may support Wi-Fi (e.g., an 802.11 protocol), Ethernet, Bluetooth, high frequency systems (e.g., 900 MHZ, 2.4 GHZ, and 5.6 GHZ communication systems), infrared, transmission control protocol/internet protocol ("TCP/1P") (e. g., any of the protocols used in each of the TCP/IP layers), hypertext transfer protocol ("HTTP"), BitTorrent, file transfer protocol ("FTP"), real-time transport protocol ("RTP"), real-time streaming protocol ("RTSP"), secure shell protocol ("SSH"), any other communications protocol, or any combination thereof. A communication interface of a system may also include circuitry that enables the system to be electrically coupled to another device and communicate with that other device.

C. Hardware and Software System(s)/Module(s)

Additionally, certain embodiments are described herein as including logic or a number of routines, subroutines, applications, or instructions. These may constitute either software (e.g., code embodied on a machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules/systems/subsystems of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

D. Processor(s)

The various operations of example methods described herein may be performed, at least partially, by one or more processors. Such processors may be configured to fetch and execute instructions stored to memory. By executing these instructions, the processor can carry out various operations or functions.

The processors may be temporarily configured (e.g., by instructions or software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

E. Memory and Computer-Readable Media

Generally speaking, as used herein the phrase "memory" or "memory device" may refer to any system or device including computer-readable media ("CRM"), which may be any available media accessible by the relevant computing system for placing, keeping, and/or retrieving information (e.g., data, computer-readable instructions, program modules, etc). The CRM may be implemented in any technology, device, or group of devices included in the relevant computing system or in communication with the relevant computing system. The CRM may include volatile and/or non-volatile media, and removable and/or non-removable media. The CRM may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store information and which can be accessed by the computing system. The CRM may be communicatively coupled to a system bus, enabling communication between the CRM and other systems or components coupled to the system bus. In some implementations the CRM may be coupled to the system bus via a memory interface (e.g., a memory controller). A memory interface is a circuit that manages the flow of data between the CRM and the system bus.

F. System Bus(es)

Generally speaking, a processor or a particular system or subsystem may communicate with other components of the system or subsystem via one or more communication links. When communicating with components in a shared housing, for example, the processor may be communicatively connected to the components by a system bus. Unless stated otherwise, as used herein the phrase "system bus" refers to: a data bus (for carrying data), an address bus (for determining where the data should be sent), a control bus (for determining the operation to execute), or some combination thereof. Further, "system bus" may refer to any of several types of bus structures including a memory bus or memory controller, a peripheral bus, or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

G. Data/Information Generation and Manipulation

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

H. Embodiments

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

I. Relational and Logical Expressions

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

Although this detailed description contemplates various embodiments, it should be understood that the legal scope of the invention is defined by the words of the claims set forth at the end of this patent. This detailed description is to be construed as exemplary only and does not describe every possible embodiment, as describing every possible embodiment would be impractical, if not impossible. One could implement numerous alternate embodiments, using either current technology or technology developed after the filing date of this patent, which may fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims of this patent is referred to in this patent in a manner consistent with a single meaning, that is done for sake of clarity only so as to not confuse the reader, and it is not intended that such claim term be limited, by implication or otherwise, to that single meaning.

The invention claimed is:

1. A method for seamlessly providing health-related information to an end-user, the method comprising:
    identifying, at one or more servers, a patient presentation for the end-user, the patient presentation being associated with (i) a set of rules and (ii) a plurality of nodes, wherein each of at least some of the plurality of nodes is selectively activated, or selectively not activated, for a particular instance of the patient presentation in accordance with the set of rules when operating upon a set of facts, and corresponds to one or more respective content assets that are to be presented to the end-user if and only if the node is activated;

determining, at the one or more servers, a first node sequence to be activated for a first instance of the patient presentation, the first node sequence including a first subset of the plurality of nodes;

identifying, at the one or more servers and based on at least the first node sequence, first content that is to be at least partially presented to the end-user during a first portion of the first instance of the patient presentation, the first content including the respective content assets that correspond to the first subset of the plurality of nodes;

sending, from the one or more servers, the first content to a client device via a network;

receiving, at the one or more servers and from the client device, a message indicating when the client device is ready for additional content of the patient presentation;

determining, at the one or more servers and using at least (i) a first rule of the set of rules and (ii) a first fact of the set of facts, a second node sequence to be activated for the first instance of the patient presentation, the second node sequence including a second subset of the plurality of nodes;

identifying, at the one or more servers and based on at least the second node sequence, second content that is to be at least partially presented to the end-user during a second portion of the first instance of the patient presentation, the second content including at least a portion of the respective content assets that correspond to the second subset of the plurality of nodes; and sending, from the one or more servers and after receiving the message, the second content to the client device via the network.

2. The method of claim 1, wherein:

identifying first content that is to be at least partially presented to the end-user includes identifying first content that includes (i) the respective content assets that correspond to the first subset of the plurality of nodes, (ii) the respective content asset or assets that correspond to at least a starting node of the second node sequence, and (iii) the respective content asset or assets that correspond to at least a starting node of a third node sequence;

determining a second node sequence to be activated for the first instance of the patient presentation includes determining that the third node sequence is not to be activated for the first instance of the patient presentation; and identifying second content that is to be at least partially presented to the end-user includes identifying second content that (i) includes a portion of the respective content assets that correspond to the second subset of the plurality of nodes, but (ii) omits at least the respective content asset or assets that correspond to the starting node of the second node sequence.

3. The method of claim 2, wherein:

determining a first node sequence to be activated for a first instance of the patient presentation includes determining a first node sequence that ends at a decision point at which one or more conditions are evaluated, the starting node of the second node sequence corresponding to an evaluation of the one or more conditions producing a first result and the starting node of the third node sequence corresponding to the evaluation of the one or more conditions producing a second result.

4. The method of claim 1, wherein:

sending the first content to the client device further includes sending first HTML5 instructions to the client device, the first HTML5 instructions including instructions for presenting the first content at the client device; and sending the second content to the client device further includes sending second HTML5 instructions to the client device, the second HTML5 instructions including instructions for presenting the second content at the client device.

5. The method of claim 1, wherein:

determining a first node sequence to be activated for a first instance of the patient presentation includes determining the first node sequence at a rules engine server of the one or more servers;

identifying first content that is to be at least partially presented to the end-user includes identifying the first content at a content server of the one or more servers, the content server being a different one of the one or more servers than the rules engine server;

sending the first content to the client device includes sending the first content from the content server to the client device;

receiving a message indicating when the client device is ready for additional content includes receiving the message at the content server;

determining a second node sequence to be activated for the first instance of the patient presentation includes determining the second node sequence at the rules engine server;

identifying second content that is to be at least partially presented to the end-user includes identifying the second content at the content server; and sending the second content to the client device includes sending the second content from the content server to the client device.

6. The method of claim 1, wherein the first subset of the plurality of nodes includes a node that, when activated, causes the client device to present a user prompt to the end-user, and wherein the method further comprises:

receiving, at the one or more servers from the client device, first data indicative of an input made by the end-user at the client device in response to the user prompt; and prior to determining the second node sequence, defining, by the one or more servers, at least the first fact according to the input made by the end-user.

7. The method of claim 1, wherein determining the second node sequence to be activated for the first instance of the patient presentation is performed by the one or more servers prior to receiving the message indicating when the client device is ready for additional content.

8. The method of claim 1, wherein one or both of:

identifying first content includes identifying first content that includes a first set of visual and audio elements; and identifying second content includes identifying second content that includes a second set of visual and audio elements.

9. The method of claim 1, wherein sending the first content to a client device includes sending the first content to a mobile device.

10. A system for seamlessly providing health-related information to an end-user, the system comprising:
one or more processors;
one or more memories storing instructions that, when executed by the one or more processors, cause the one or more processors to
identify a patient presentation for the end-user, the patient presentation being associated with (i) a set of rules and (ii) a plurality of nodes, wherein each of at least some of the plurality of nodes
is selectively activated, or selectively not activated, for a particular instance of the patient presentation in accordance with the set of rules when operating upon a set of facts, and
corresponds to one or more respective content assets that are to be presented to the end-user if and only if the node is activated,
determine a first node sequence to be activated for a first instance of the patient presentation, the first node sequence including a first subset of the plurality of nodes,
identify, based on at least the first node sequence, first content that is to be at least partially presented to the end-user during a first portion of the first instance of the patient presentation, the first content including the respective content assets that correspond to the first subset of the plurality of nodes,
send the first content to a client device via a network,
receive from the client device a message indicating that the client device is ready for additional content of the patient presentation,
determine, using at least (i) a first rule of the set of rules and (ii) a first fact of the set of facts, a second node sequence to be activated for the first instance of the patient presentation, the second node sequence including a second subset of the plurality of nodes,
identify, based on at least the second node sequence, second content that is to be at least partially presented to the end-user during a second portion of the first instance of the patient presentation, the second content including at least a portion of the respective content assets that correspond to the second subset of the plurality of nodes, and
send the second content to the client device via the network.

11. The system of claim 10, wherein:
the identified first content includes (i) the respective content assets that correspond to the first subset of the plurality of nodes, (ii) the respective content asset or assets that correspond to at least a starting node of the second node sequence, and (iii) the respective content asset or assets that correspond to at least a starting node of a third node sequence;
the instructions cause the one or more processors to, in addition to determining a second node sequence to be activated for the first instance of the patient presentation, determine that the third node sequence is not to be activated for the first instance of the patient presentation; and
the identified second content (i) includes a portion of the respective content assets that correspond to the second subset of the plurality of nodes, but (ii) omits at least the respective content asset or assets that correspond to the starting node of the second node sequence.

12. The system of claim 11, wherein:
the first node sequence ends at a decision point at which one or more conditions are evaluated;
the starting node of the second node sequence corresponds to an evaluation of the one or more conditions producing a first result; and
the starting node of the third node sequence corresponding to the evaluation of the one or more conditions producing a second result.

13. The system of claim 10, wherein the instructions are configured to:
send first HTML5 instructions to the client device with the first content, the first HTML5 instructions including instructions for presenting the first content at the client device; and
send second HTML5 instructions to the client device with the second content, the second HTML5 instructions including instructions for presenting the second content at the client device.

14. The system of claim 10, wherein:
the first subset of the plurality of nodes includes a node that, when activated, causes the client device to present a user prompt to the end-user; and
the instructions further cause the one or more processors to
receive, from the client device, first data indicative of an input made by the end-user at the client device in response to the user prompt, and
prior to determining the second node sequence, define at least the first fact according to the input made by the end-user.

15. The system of claim 10, wherein one or both of:
the first content includes a first set of visual and audio elements; and
the second content includes a second set of visual and audio elements.

16. A system comprising:
a client device associated with an end-user;
a first data storage storing a knowledge base that includes a set of rules and a set of facts both associated with a patient presentation;
a second data storage storing a plurality of content assets for a plurality of nodes associated with the patient presentation, wherein each of at least some of the plurality of nodes (i) is selectively activated, or selectively not activated, for a particular presentation of the patient presentation in accordance with the set of rules when operating upon the set of facts, and (ii) corresponds to one or more respective content assets, of the plurality of content assets, that are to be presented to the end-user if and only if the node is activated; and
one or more servers configured to (i) determine a first node sequence to be activated for a first instance of the patient presentation, the first node sequence including a first subset of the plurality of nodes, (ii) identify, based on at least the first node sequence, first content that is to be at least partially presented to the end-user during a first portion of the first instance of the patient presentation, the first content including the respective content assets that correspond to the first subset of the plurality of nodes, and (iii) send the first content to the client device via a network,
wherein the client device is configured to (i) assemble the first content during the first instance of the patient presentation, (ii) present at least a portion of the assembled first content to the end-user, and (iii) prior to an entirety of the portion of the first content being presented to the end-user, send the one or more servers a message indicating when the client device is ready for additional content of the patient presentation, wherein the one or more servers are further configured to, after receiving the message indicating when the client device is ready for additional content, (i) determine, using at least a first rule of the set of rules and a first fact of the set of facts, a second node sequence to be activated for the first instance of the patient presentation, the second node sequence including a second subset of the plurality of nodes, (ii) identify, based on at least the second node sequence, second content that is to be at least partially presented to the end-user during a second portion of the first instance of the patient presentation, the second content including at least a portion of the respective content assets that correspond to the second subset of the plurality of nodes, and (iii) send the second content to the client device via the network, and wherein the client device is further configured to (i) assemble the second content during the first instance of the patient presentation, and (ii) present at least a portion of the assembled second content to the end-user.

17. The system of claim 16, wherein the client device is a mobile device having a display device, a speaker, and one or more input devices.

18. The system of claim 16, wherein the client device is configured to present at least the portion of the first content, and at least the portion of the second content, to the end-user via an HTML5-capable web browser.

19. The system of claim 16, wherein the client device is configured to execute a multi-thread process, the multi-thread process including (i) a first thread for producing content, the first thread generating the message indicating when the client device is ready for additional content, and (ii) a second thread for consuming content, the second thread assembling the first content and the second content substantially in real-time as the first content and the second content, respectively, are received by the client device.

20. The system of claim 16, wherein the message indicating when the client device is ready for additional content includes either (i) a message requesting additional content, or (ii) a message causing the one or more servers to refrain from sending additional content for a predetermined time period.

* * * * *